United States Patent
Su et al.

(10) Patent No.: US 7,294,715 B2
(45) Date of Patent: Nov. 13, 2007

(54) APORPHINE AND OXOAPORPHINE COMPOUNDS AND PHARMACEUTICAL USE THEREOF

(75) Inventors: Mingjai Su, Taipei County (TW); Shoeisheng Lee, Taipei (TW)

(73) Assignee: Lotus Pharmaceutical Co., Ltd., Taipei (TW)

( * ) Notice: Subject to any disclaimer, the term of this patent is extended or adjusted under 35 U.S.C. 154(b) by 0 days.

(21) Appl. No.: 11/439,076

(22) Filed: May 23, 2006

(65) Prior Publication Data

US 2006/0211723 A1   Sep. 21, 2006

Related U.S. Application Data

(63) Continuation-in-part of application No. 10/817,641, filed on Apr. 2, 2004, now Pat. No. 7,057,044.

(60) Provisional application No. 60/693,031, filed on Jun. 22, 2005.

(30) Foreign Application Priority Data

| Apr. 4, 2003 | (TW) | ................ 92107780 A |
| Jun. 19, 2003 | (CN) | .................. 03137381 |
| Jun. 19, 2003 | (WO) | ............ PCT/CN03/00477 |

(51) Int. Cl.
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |

(52) U.S. Cl. ........................................ 546/41
(58) Field of Classification Search ................. 546/61, 546/41, 42, 58; 514/284
See application file for complete search history.

(56) References Cited

U.S. PATENT DOCUMENTS 6,313,134 B1 * 11/2001 Su et al. ....................... 514/284

OTHER PUBLICATIONS

Lan et al., J.Nat.Prod.,"Cytotoxic styrylpyrones form Goniothalamus amuyon",2003, vol. 66, pp. 487-490.*
Zhang et al., Chem.Pharm.Bull.,"Sesquiterpenes and alkoloids from Lindera chunii and their inhibitory activities against HIV-1 integrase", 2002, vol. 50,pp. 1195-1200.*
Khroyan et al., J. of Pharmacology and Experimental Therapeutics, "Dopamine D1-and D2Like receptor mechanisms in relapse to cocaineseeking behaviour: effects of selective antagonists and agonists", 2003, vol. 66,pp. 680-687.*
Chiou et al., J.Nat.Prod., "Litebamine N-homologues: preparation and anti-acetylcholinesterase activity", 1998,vol. 61,pp. 46-50.*
Lee et al., Tetrahedron Letters, "preparation of phenanthrene alkaloids via solvolysis of 2-hydroxyaporphines"1995,vol. 36,pp. 1531-1532.*
Hsieh et al., J.Nat.Prod., "The alkaloids of *Artabotrys uncinatus*",2001,vol. 64, pp. 1157-1161.*
Matteo et al., J.Am.Chem.Soc.,"Correlation between molecular structure and helicity of induced chiral nematics in terms of short-range and electrostatic-induction interactions. The case of chiral biphenyls",2001,vol. 123,pp. 7842-7851.*
Ribeiro et al., Phtomedicine,"In vitro dose dependent inverse effect of nantenine on synaptosomal membrane K-p-NPPase activity",2001, vol. 8,pp. 107-111.*
Sun et al., Journla of pharmaceutical and Biomedical analysis, "Determination of *Lauraceous aporphine* alkaloids by high-performane liquid chromatography",1996,vol. 14,pp. 1383-1387.*
Chen et al., Planta Medica, "Cytotoxic constituents from *Aquilegia ecalcarata*",2002,vol. 68, pp. 554-556.*
Jantan et al., Planta Medica, "Inhibition of plantelet-activating factor receptor binfing by aporphine and phenanthrenoid alkaloids from aromadendron elegans",2001,vol. 7, pp. 466-467.*
Nissanka et al., Phytochemistry, "Antimicrobial alkaloids from *Zanthoxylum tetraspermum* and *caudatum*", 2001,vol. 56,pp. 857-861.*

* cited by examiner

*Primary Examiner*—Margaret D Seaman
*Assistant Examiner*—Niloofar Rahmani
(74) *Attorney, Agent, or Firm*—Osha Liang LLP

(57) ABSTRACT

The invention provides aporphine and oxoaporphine compounds that may be used to manufacture a medicaments for preventing or treating vascular dysfunctions that may result in ischemic and metabolic diseases or preventing complications associated with these diseases in human and mammal. The ischemic diseases may include ischemic cerebral apoplexy, ischemic cerebral thrombosis, ischemic cerebral embolism, hypoxic ischemic encephlopathy, ischemic cardiac disease or ischemic enteropathy etc. The metabolic disease may include diabetes-induced vascular diseases, such as hypertension, atherosclerosis, peripheral artery or venous thrombosis, retinopathy and nephropathy. Methods for treating ischemic and metabolic diseases or preventing complications are also disclosed.

9 Claims, 4 Drawing Sheets

| Formula | A | A | B | A | A |
|---|---|---|---|---|---|
| Number | 16 | 20 | 21 | 8 | 9 |
| Substitution | $R_1$=OH, $R_3$=$R_5$=$R_8$=H, $R_2$=$R_5$=$R_7$=OMe, $R_2$=2-(2-methoxyphenoxy)ethyl | $R_1$=OH, $R_4$=Me, $R_2$=$R_6$=$R_7$=OMe, $R_3$=$R_5$=$R_8$=H | $R_1$=$R_2$=$R_5$=$R_6$=OMe, $R_3$=$R_4$=$R_7$=H | $R_1$&$R_2$=-OCH$_2$O-, $R_3$=$R_4$=$R_5$=$R_8$=H, $R_6$=OMe, $R_7$=OH | $R_1$=OMe, $R_2$=OH, $R_3$=$R_5$=$R_8$=H, $R_4$=Me, $R_6$&$R_7$=-OCH$_2$O- |
| conc. (μM) | Coronary flow (ml/min) | n | coronary flow (ml/min) | n | coronary flow (ml/min) | n | coronary flow (ml/min) | n | coronary flow (ml/min) | n |
| 0 | 9.4 ± 0.5 | 3 | 13.8 ± 0.9 | 4 | 11.4 ± 0.6 | 4 | 9.1 ± 0.6 | 4 | 9.4 ± 0.5 | 3 |
| 0.1 | 9.5 ± 0.9 | 3 | 14.9 ± 0.5 | 4 | 12.5 ± 1.1 | 4 | 9.4 ± 0.6 | 4 | 9.5 ± 0.9 | 3 |
| 0.3 | 9.7 ± 1.1 | 3 | 15.3 ± 0.6 * | 4 | 13.7 ± 0.8 * | 4 | 9.4 ± 0.6 | 4 | 9.7 ± 1.1 | 3 |
| 1 | 9.5 ± 0.8 | 3 | 17.6 ± 0.9 * | 4 | 18.5 ± 0.7 * | 4 | 9.3 ± 0.8 | 4 | 9.5 ± 0.8 | 3 |
| 3 | 9.7 ± 0.6 | 3 | 18.9 ± 1.0 * | 4 | 21.2 ± 0.8 * | 4 | 10.3 ± 0.9 | 4 | 9.7 ± 0.6 | 3 |
| 10 | 13.1 ± 1.3* | 3 | 21.4 ± 1.3 | 3 | | | 17.6 ± 1.7 * | 4 | 13.1 ± 1.3 * | 3 |

\* indcates P < 0.05, compared with the untreated control.

Effects on Coronary Flow in Ischemia-Reperfused Wistar Rat Hearts

FIG. 3

APORPHINE AND OXOAPORPHINE COMPOUNDS AND PHARMACEUTICAL USE THEREOF

CROSS-REFERENCE TO RELATED APPLICATIONS

This is a Continuation-In-Part application and claims benefit of U.S. application Ser. No. 10/817,641, filed on Apr. 2, 2004 now U.S. Pat. No. 7,057,044, which claims priority from Taiwanese Application No. TW92107780 filed on Apr. 4, 2003, Chinese Application No. 03137381.X filed on Jun. 19, 2003, and PCT Application No. PCT/CN03/00477 filed on Jun. 19, 2003. This also claims priority of U.S. Provisional Application Ser. No. 60/693,031 filed on Jun. 22, 2005. The '641 and '031 applications are incorporated by reference in their entireties.

BACKGROUND OF INVENTION

1. Field of the Invention

The present invention relates to compounds for maintaining the vascular function to treat or prevent the ischemic and metabolic diseases, more particularly to aporphine and oxoaporphine compounds that can be used to preserve the vascular endothelial function to prevent or treat ischemic and metabolic diseases.

2. Background of the Invention

With the progress of society and the advance in sciences and technology, life expectancy gradually increases. Many people now suffer from various diseases due to old age, diet, obesity, lack of exercise or living under stress. Among these diseases, ischemic diseases are among the main causes of death and physical impairment. Ischemic and metabolic diseases have a major impact and cause substantial loss to people, family, society and the state. Therefore, it is important to find agents to prevent the ischemic and metabolic diseases.

Among ischemic diseases, vascular damage, particularly endothelial dysfunction is a major abnormality presented in varying degrees at different stages. The endothelial layer in vessels provides a critical interface between the elements of blood and tissues. A healthy endothelial layer provides a smooth, quiescent surface that limits the activation of clotting and proinflammatory factors, blocks the transfer of atherogenic lipid particles into the arterial wall, and prevents adhesion of platelets and monocytes to the vascular endothelials. Vascular endothelial dysfunction, therefore, may occur at any or all levels in the arterial system and may contribute to the development and progression of atherosclerosis by favoring coagulation, cell adhesion and inflammation, by promoting inappropriate vasoconstriction and/or vasodilatation, and by enhancing transendothelial transport of atherogenic lipoproteins. Atherosclerosis may lead to the development of cardiac or cerebral diseases even though atherosclerosis occurs in the coronary or intracranial arteries.

Vascular dysfunction also plays a role in the progression of metabolic diseases, because coronary atherosclerosis is responsible for the vast majority of the cardiovascular events, which occur with increased frequency in individuals with hypertension hyperlipidemia, obesity, diabetes and renal disease. A number of cardiovascular risk factors, including coronary artery disease, hypertension, hypertriglyceridemia and visceral obesity have been collectively termed the metabolic syndrome. The metabolic syndrome is typically associated with endothelial dysfunction and insulin resistance, which is the major characteristic of Type II diabetes. Endothelial dysfunction contributes to impaired insulin action by altering the transcapillary passage of insulin to target tissues. Reduced expansion of the capillary network, with attenuation of microcirculatory blood flow to metabolic active tissues, contributes to the impairment of insulin-stimulated glucose and lipid metabolism. This establishes a negative feedback cycle in which progressive endothelial dysfunction and disturbances in glucose and lipid metabolism develop secondary to the insulin resistance. Vascular damage, which results from lipid deposition and oxidative stress to the vessel wall, triggers an inflammatory reaction, and the release of chemo attractants and cytokines worsens the insulin resistance and endothelial dysfunction.

There have been many studies focused on the endothelial function to prevent the vascular endothelial damage. The role of nitric oxide (NO), a vasodilator synthesized by endothelial nitric oxide synthase (eNOS), has been extensively studied in recent years. Many studies indicated that various drugs with different mechanisms for the management of cardiovascular and metabolic diseases, such as statins, PDE5 inhibitors, ACE inhibitors, may limit ischemic or ischemia-reperfusion injuries by enhancing NO or eNOS activity. (Journal of Molecular and Cellular Cardiology, 2006, 40(1), 16-23.) The abnormalities of nitric oxide (NO) release and endothelial nitric oxide synthase (eNOS) system have been shown to provide the link between insulin resistance and endothelial dysfunction. (Diabetes/Metabolism Research and Reviews, Feb. 28, 2006.) Therefore, compounds capable of maintaining or increasing endothelial nitric oxide synthase (eNOS) activities, should preserve vascular endothelial functions and can be used not only to prevent the ischemic diseases, but also to improve the insulin resistance to activate the glucose utility in tissues, leading to lowered blood sugar level. It is desirable to have compounds that can be used in the prevention and treatment of vascular dysfunction resulting in ischemic and metabolic diseases.

SUMMARY OF THE INVENTION

One object of the invention is to provide aporphine and oxoaporphine compounds that can be used in the prevention and treatment of vascular dysfunctions that may cause ischemic and metabolic diseases and associated complications to the tissues or organs.

Embodiments of the present invention relate to certain aporphine and oxoaporphine compounds that can preserve the activity of endothelial nitric oxide synthase (eNOS), which produces nitric oxide (NO) to dilate blood vessels. Such aporphine and oxoaporphine compounds are more effective in opening up blocked vessels than conventional clot dissolving agents and can maintain the vascular function to increase blood flows to the ischemic tissues. As compared with MK801, these aporphine and oxoaporphine compounds will not cause memory loss or hypothermic side effects when they are used to treat ischemic diseases. Other agents of this class of compounds act as modulators of vasoconstriction and are therefore capable of restoring normal heart rhythms and improving the vascular circulation. In such a capacity, aporphine and oxoaporphine derivatives of the present invention show promise as therapeutic agents for preventing complications induced by ischemic or metabolic diseases, such as arrhythmias, including ventricular tachycardia and ventricular fibrillation, or diabetes associated vascular syndromes, including retinopathy and nephropathy.

To achieve the above-described objectives, some embodiments of the present invention provide aporphine compounds for the prevention and treatment of vascular dysfunctions that may result in ischemic and metabolic diseases or for the prevention of complications that are associated with these diseases. Aporphine compounds in accordance with embodiments of the invention have the following structure:

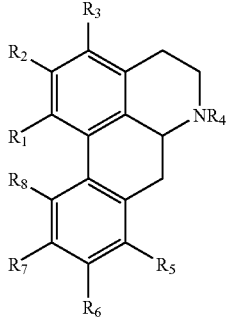

Formula A (Aporphine)

wherein $R_1$, $R_2$, $R_6$ and $R_7$ are each selected from H, OH, O-acyl, OMe, OEt, O"Pr and O$^i$Pr, or $R_1$ and $R_2$ jointly form —OCH$_2$O—, or $R_6$ and $R_7$ jointly form —OCH$_2$O—, wherein $R_3$ and $R_5$ are each selected from H, OH, O-acyl, OMe, F, Cl, Br, NH$_2$, NO$_2$ and CN; $R_8$ is selected from H, OH, and OMe; and $R_4$ is selected from allyl and $C_nH_{2n+1}$, $n \geq 0$; or $R_4$ is an alkylaryl group, wherein the alkylaryl group is a short alkyl group with an aryl group attached to one end. Examples of an alkylaryl group may include:

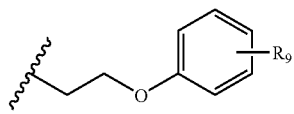

wherein $R_9$ is H, OH, OMe, NO$_2$, halide, or OAc;

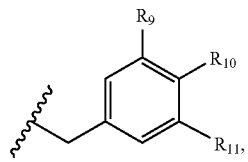

wherein $R_9$, $R_{10}$, $R_{11}$ are independently H, OH, OMe, NO$_2$, halide, OAc, or alkyl;

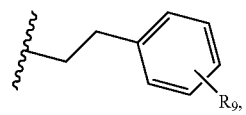

wherein $R_9$ is H, OH, OMe, NO$_2$, halide, or OAc; and

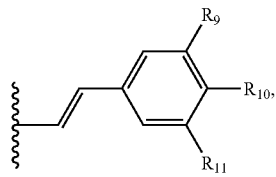

wherein $R_9$, $R_{10}$, $R_{11}$ are independently H, OH, OMe, NO$_2$, or OAc.

Some embodiments of the present invention provide oxoaporphine compounds for the prevention and treatment of vascular dysfunction that may result in ischemic and metabolic diseases or for preventing complications that are associated with these diseases. An oxoaporphine compound in accordance with embodiments of the invention has the following structure:

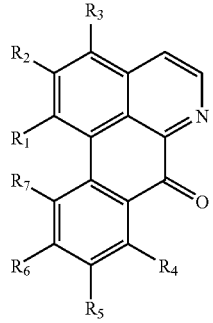

Formula B (Oxoaporphine)

where $R_1$, $R_2$, $R_5$ and $R_6$ are each selected from H, OH, O-acyl, OMe, OEt, O"Pr and O$^i$Pr, or $R_1$ and $R_2$ jointly form —OCH$_2$O—, or $R_5$ and $R_6$ jointly form —OCH$_2$O—; $R_3$ and $R_4$ are each selected from H, OH, O-acyl, OMe, F, Cl, Br, NO$_2$ and CN; and $R_7$ is selected from H, OH, O-acyl, and OMe.

Some embodiments of the invention relate to use of the aporphine or oxoaporphine compounds in the manufacture of medicaments for treating vascular dysfunction that may result in ischemic and metabolic diseases or for preventing complications associated with these diseases in mammal or human beings. Ischemic diseases, for example, include ischemic cerebral apoplexy, ischemic cerebral thrombosis, ischemic cerebral embolism, hypoxia and ischemic encephalopathy, ischemic cardiac disease, ischemic enteropathy, peripheral ischemia disease, ischemic reperfusion induced arrhythmias and the like. Metabolic diseases and the associated complications, for example, may include hypertension, atherosclerosis, hyperglycemia and diabetes-induced vascular diseases, including peripheral artery or venous thrombosis, erectile dysfunction, retinopathy or nephropathy.

Embodiments of the present invention also relate to methods of using aporphine or oxoaporphine compounds in the prophylaxis or treatment of ischemic and metabolic diseases, and the use of aporphine and oxoaporphine compounds in the prophylaxis or treatment of ischemic and metabolic diseases in mammal and human beings.

Embodiments of the invention also relate to pharmaceutical compositions for the prophylaxis or treatment of ischemic and metabolic diseases. A pharmaceutical composition in accordance with embodiments of the invention comprises a therapeutically effective amount of aporphine or oxoaporphine compounds and a pharmaceutically acceptable carrier or excipient. One of ordinary skill in the art would appreciate that "an effective amount" refers to an amount sufficient to achieve the prevention or treatment of an ischemic or metabolic disease. The specific amount will depend on the age, body weight of the patient and the status of disease/damage.

The following examples and the associated figures further describe and demonstrate embodiments of the present invention. These examples are given solely for illustration and are not intended to limit the scope of the invention to these illustrated examples.

BRIEF DESCRIPTION OF THE DRAWINGS

FIG. 3 shows the enhancement of coronary flows of various aporphine and oxoaporphine compounds in Langendorff perfused rat hearts.

DETAILED DESCRIPTION OF THE INVENTION

Figure 1A:
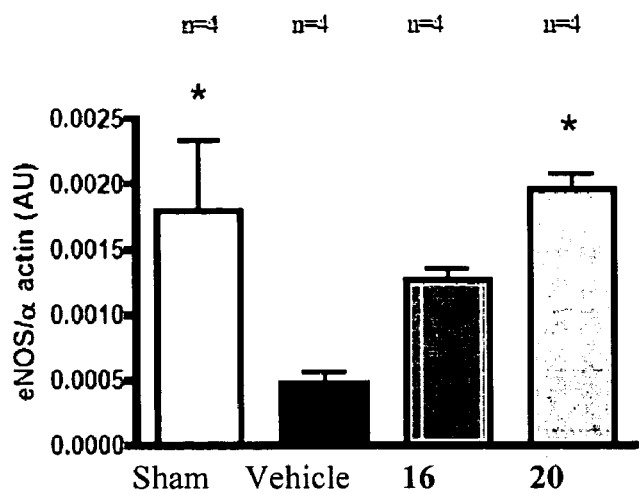
FIG. 1A-1C shows effects of Compound 16 and Compound 20 on eNOS protein expression and the infarct size in a rat heart that had suffered ischemia for 25 min and was then reperfused for 2-hr.

Human blood vessels can synthesize nitric oxide (NO). NO can dilate blood vessels and, therefore, NO production is closely associated with blood pressure regulation. Endogenous NO plays an important role in the vascular smooth muscle relaxation. In ex vivo experiments using an isolated aortic ring and local blood vessel layer and in vivo whole body experiments have shown that the blood vessels constrict and the blood pressures elevate upon the interruption of NO formation. In mammals, NO is synthesized from L-arginine by nitric oxide synthase (NOS). The NOS converts L-arginine to an intermediate, which is then converted to L-citrulline and NO as follows:

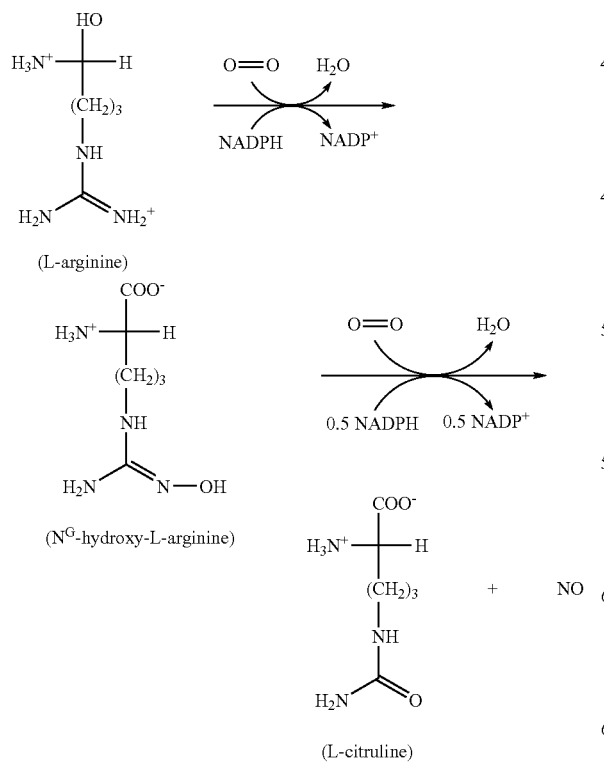

NOS exists in at least three isoforms, including neuronal NOS (nNOS, or type I NOS), inducible NOS (iNOS, or type II NOS), and endothelial NOS (eNOS, or type III NOS). Among these, the function of eNOS is responsible for the regulation of blood vessel tension. The function and mechanism of NO as a signal transduction messenger vary depending on where it is produced. NO has three major functions: (1) in nerve synapse, NO is released as neurotransmitter which regulates brain learning and memory; (2) in blood vessel endothelia, NO relaxes vascular smooth muscle, dilates the vessel, and lowers blood pressure; and (3) in macrophage, NO destroys and kills tumor cells or foreign pathogens.

nNOS and eNOS are complex enzymes, requiring calcium and calmodulin. Calcium first binds to calmodulin, then the calcium-calmodulin complex binds nNOS or eNOS to activate its catalytic activity. On the other hand, iNOS is inducible and does not depend on calcium or calmodulin. Instead, iNOS is induced by cytokines. Because iNOS is calcium-independent and calmodulin-independent, the activity of iNOS once induced cannot be easily terminated and may last for several hours, leading to overproduction of NO, which can be harmful.

Prior to the present invention, research on compounds that can maintain or increase eNOS activities is mostly focused on the treatment of cardiovascular diseases (e.g., arrhythmia, Su M J, et al., Drug Development Research, 2001, 52:446-453). The present invention provides new compounds that function by a similar mechanism but can be used to prevent or treat ischemic diseases, such as stroke, and metabolic diseases, such as diabetes vascular disorders. The following describes methods and results of using these compounds in the treatment of above diseases.

The invention relates to aporphine and oxoaporphine compounds for use in preventing or treating vascular dysfunction that may result in ischemic and metabolic diseases. These compounds function by maintaining or increasing endothelial nitric oxide synthase (eNOS) activities. Two examples of aporphine compounds of Formula A are Compound 16, where $R_1$, $R_2$, $R_6$, $R_7$ are OMe, $R_3$, $R_5$ and $R_8$ are H, and $R_9$=2-OMe in the $R_4$ as 2-phenoxyethyl group, and Compound 20, where $R_1$ is OH, $R_2$, $R_6$, $R_7$ are OMe, $R_3$, $R_5$, $R_8$ are H, and $R_4$ is Me. The structures of Compound 16 and Compound 20 are as follows:

Compound 16

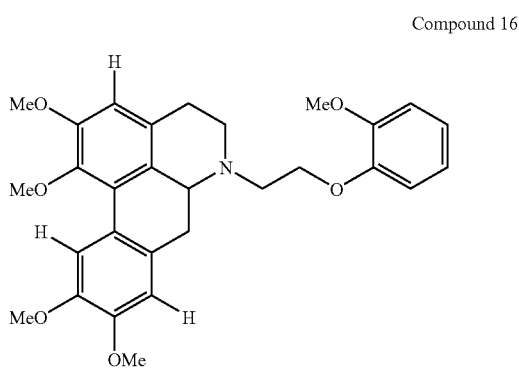

-continued

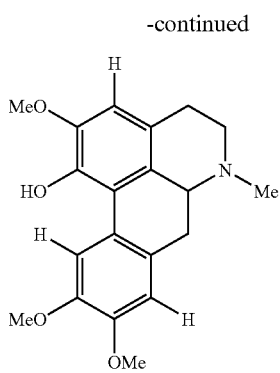

Compound 20

Figure 1B:
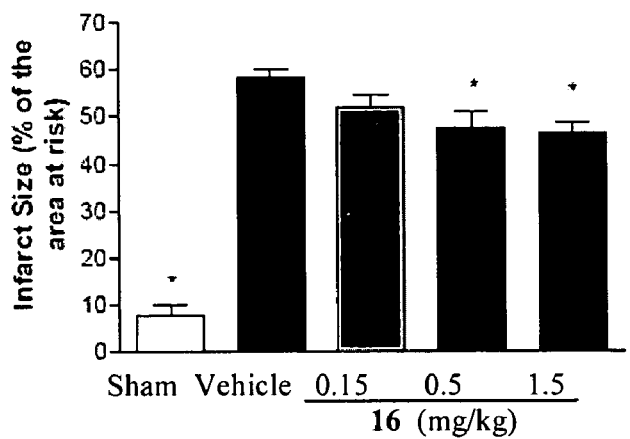

FIG. 1A and FIG. 1B show effects of Compound 16 and Compound 20 in Formula A on the protection of eNOS activity and the reduction of infarct size caused by regional myocardial ischemia and reperfusion, respectively, to achieve the aim of vascular function preservation for preventing or treating ischemic and metabolic diseases.

FIG. 1A shows the effects of Compound 16 and Compound 20 on eNOS protein expression in a rat heart that had suffered from ischemia for 25 min and then was reperfused for 2-hrs. When compared to sham operated rats, ischemia and reperfusion of the rat heart caused a significant reduction in eNOS protein expression. The reduction in eNOS protein expression was significantly reduced by the administration of Compound 16 (1.5 mg/kg) and Compound 20 (0.5 mg/kg) at 5 min prior to reperfusion (P<0.05, when compared to vehicle). By comparing the expression levels of eNOS, it is clear that the expression levels of eNOS in the ischemia-reperfusion hearts can approach the normal value after treatment with Compound 16 or Compound 20. These results show that a compound of the present invention can improve the expression of eNOS or maintain its expression at a constant level. Therefore a compound of the invention can preserve the endothelial function and prevent the vascular dysfunction.

Figure 1C:
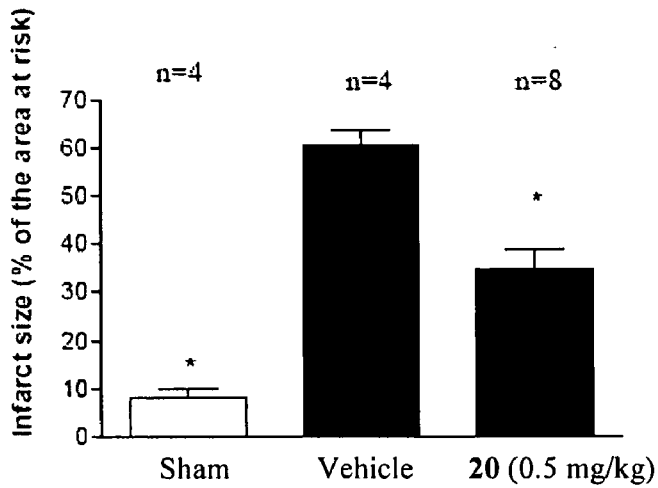

The aporphine and oxoaporphine compounds of the invention have been also found to be effective in preventing damages resulting from ischemia reperfusion due to its ability to preserve eNOS activity. As shown in FIG. 1B, rats treated with vehicle (0.25% L-tartaric acid and 5%glucose), occlusion of the LAD (for 25 min) followed by reperfusion (for 2 h) resulted in an infarct size of 58±2% of the area at risk. Intravenous administration of Compound 16 (0.5 mg/kg) reduced the infarct size from 58±2% to 47±4% of the area at risk (P<0.05, as compared to vehicle group). Further, the intravenous administration of a higher dose of Compound 16 (1.5 mg/kg) reduced the infarct size to 47±2% of the area at risk (P<0.05, as compared to vehicle group). In FIG. 1C, the intravenous administration of the highest dose of Compound 20 (0.5 mg/kg) reduced the infarct size to 34±4% of the area at risk (P<0.05, when compared to vehicle saline group). The results shows the compounds of the invention are effective in preventing the ischemia-reperfusion damages.

The same effects of preventing the ischemia-reperfusion damages with aporphine and oxoaporphine compounds also found in the other organs, such as brain. After Compound 16 or Compound 21, which is a compound of Formula B (where $R_1$, $R_2$, $R_5$, $R_6$ are OMe, $R_3$, $R_4$, $R_7$ are H) was administrated to male Sprague Dawley rats, the effects of test compounds on the artery occlusive cerebral ischemia in the rats were monitored. First, permanent brain ischemia was induced by middle cerebral artery occlusion (MCAO) in the rats. At 0, 6, 24, 48, and 54 hours after the formation of middle cerebral artery occlusion (MCAO), Group I (i.e., the control group) animals were given the solvent (100% DMSO) (1 ml/kg, i.p.); Group II (i.e., the control group) animals were given the distilled water (D.W.) (1 ml/kg, i.p.);Group III animals (NCM-121) were given Compound 16 (1.5 mg/kg, i.p.); Group IV animals (NCM-124) were given Compound 21 (1.7 mg/kg, i.p); Group V animals were given MK-801 (0.3 mg/kg, i.p.), an antagonist of the N-methyl-D-aspartic acid (NMDA) receptor. There were ten rats in each group. Four days after the formation of MCAO, all the rats were sacrificed. Brain sections were made and stained with 2% cresol purple. The areas and volumes of cerebral ischemia lesions in each section were recorded.

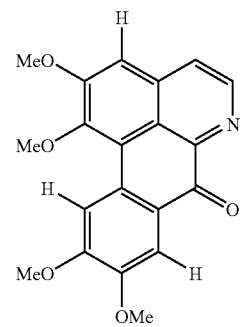

Compound 21

Figure 2A:
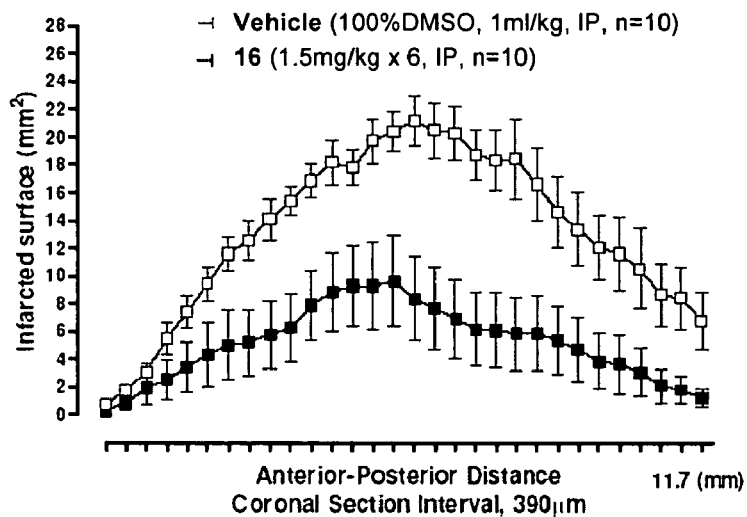
FIG. 2A-2C shows the comparative curve of results of Compound 16, Compound 21 and a reference drug on the decrease in total volume of ischemic lesions in the brains of middle cerebral artery occlusion rats.
Figure 2B:
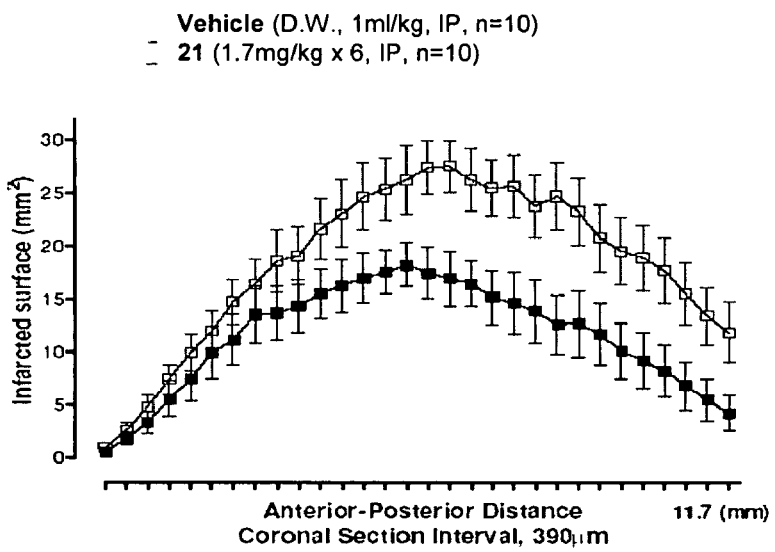
Figure 2C:
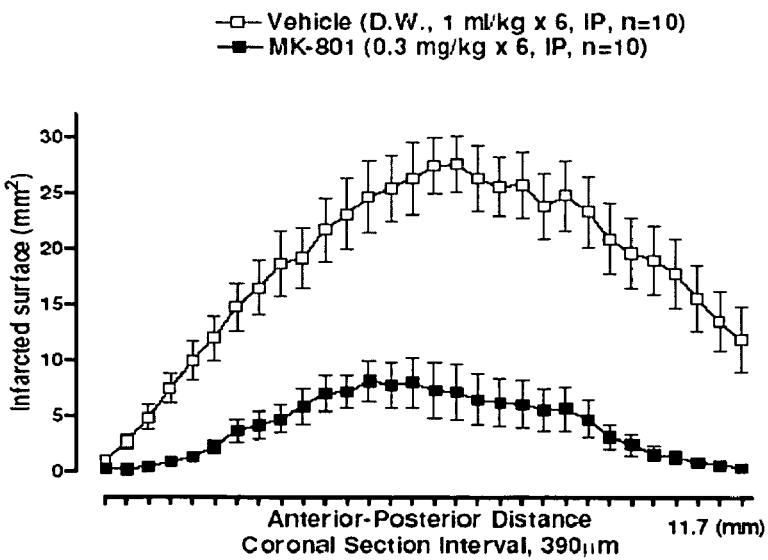

The results are shown in Table 1 for Groups I, II, III, IV and V and the comparative results among these three groups are also shown as graphs. For example, FIG. 2A shows the comparative curves of the results of group I and group III. FIG. 2B shows the comparative curves of the results of group II and group IV and FIG. 2C shows the comparative curves of the results of group II and group V. From these data, as compared with MK-801, it is apparent that the Compound 16 and Compound 21 had more significant effects in reducing the areas and volumes of cerebral ischemia lesions in the treatment of ischemic apoplexy.

TABLE 1

Calculated Decrease in Total Volume of Ischemic Lesions in the Brains of MCAO Rats by the Test Compound

| Group | Treatment | Route | Dose | N | Infarcted Volume (X ± SEM mm³) | % Decrease. (X ± SEM) |
|---|---|---|---|---|---|---|
| I | Vehicle Control (100% DMSO) | IP | 1 ml/kg × 6 | 10 | 154.17 ± 16.69 | — |

TABLE 1-continued

Calculated Decrease in Total Volume of Ischemic Lesions
in the Brains of MCAO Rats by the Test Compound

| Group | Treatment | Route | Dose | N | Infarcted Volume (X ± SEM mm$^3$) | % Decrease. (X ± SEM) |
|---|---|---|---|---|---|---|
| II | Vehicle Control (D.W.) | IP | 1 mg/kg × 6 | 10 | 214.75 ± 26.37 | — |
| III | NCM-121 | IP | 1.5 mg/kg × 6 | 10 | 60.14 ± 24.49* | 60.99 |
| IV | NCM-124 | IP | 1.7 mg/kg × 6 | 10 | 133.75 ± 19.57* | 37.72 |
| V | MK-801 | IP | 0.3 mg/kg × 6 | 10 | 47.34 ± 13.79* | 77.96 |

*P < 0.05

Figure 4:
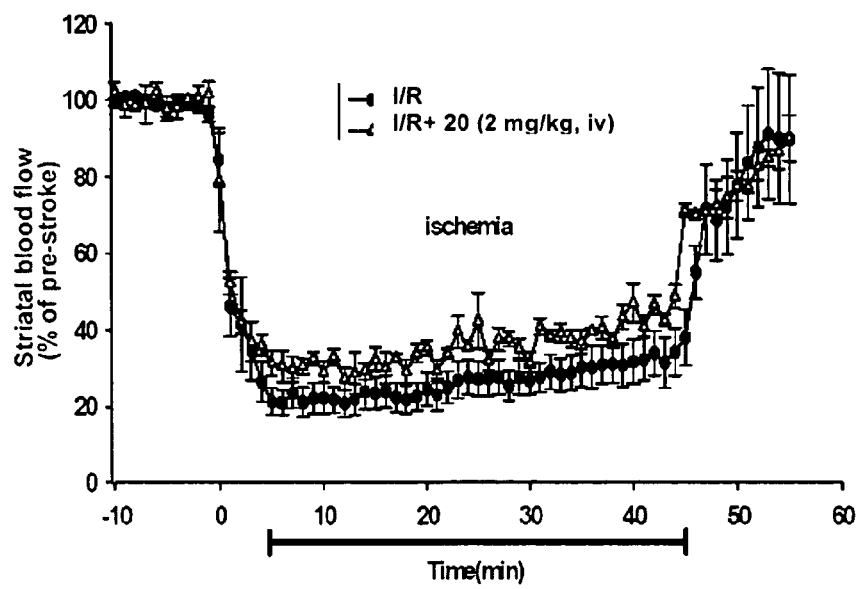
FIG. 4 shows the effect of Compound 20 on the blood flow in a rat brain that had suffered focal cerebral ischemia and 24 hr reperfusion.

Several aporphine and oxoaporphine compounds of the invention demonstrated the ability to improve the vascular function by increasing coronary blood flow of Langendorff perfused hearts. FIG. 3 shows representative results of several aporphine and oxoaporphine compounds from the Formula A and B groups, including Compound 16, 20 and 21. The increase in blood flow has been also proved in the animal model of focal cerebral ischemia-reperfusion. FIG. 4 shows the results of striatal blood flow measured by invasive laser Doppler flowmetry in male Sprague-Dawley rats subjected to unilateral 40-min occlusion of the common carotid artery in combination with ipsilateral intracerebral injection of endothelin-1 (ET-1; 120 pmol/10 μL) to cause ischemia, followed by 24-hrs reperfusion. The increase in blood flow in brain by Compound 20 demonstrated the ability of compounds of the invention to improve vascular functions in the peripheral vascular system The fact that various aporphine and oxoaporphine compounds have the ability to prevent or minimize vascular damage suggests that the active moiety in all these compounds is a common core structure. For example, the aporphine compounds above may be commonly represented by Formula A below:

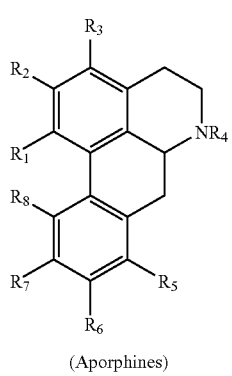

(Aporphines)

Formula A where $R_1$, $R_2$, $R_6$ and $R_7$ are each selected from H, OH, O-acyl, OMe, OEt, O$^n$Pr and O$^i$Pr, $R_3$ and $R_5$ are each selected from H, OH, O-acyl, OMe, F, Cl, Br, $NH_2$, $NO_2$ and CN; $R_8$ is selected from H, OH, and OMe; and $R_4$ is selected from allyl and $C_nH_{2n+1}$, $n \geq 0$; or $R_4$ is an alkylaryl group. An "alkylaryl" group as used herein refers to an alkyl substituent that is linked to an aryl group at one end. The alkylaryl groups preferably have an alkyl group having 1-5 carbons, more preferably 2-3 carbons, and preferably have one single aromatic ring, which may be optionally substituted. Furthermore, an "alkylaryl" group may include one or more hetero atoms substituting a carbon in the alkyl chain. Examples of alkylaryl groups are shown in the following table.

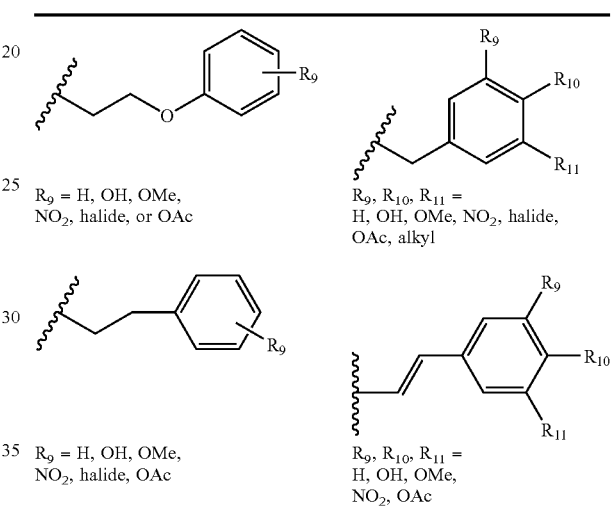

$R_9$ = H, OH, OMe, $NO_2$, halide, or OAc $R_9$, $R_{10}$, $R_{11}$ = H, OH, OMe, $NO_2$, halide, OAc, alkyl $R_9$ = H, OH, OMe, $NO_2$, halide, OAc $R_9$, $R_{10}$, $R_{11}$ = H, OH, OMe, $NO_2$, OAc Some aporphine compounds of the invention, as shown in Formula A above, may have $R_1$ and $R_2$ jointly form —OCH$_2$O—, such that they form a five membered-ring 1,3-dioxolane fused with the aromatic ring to which they are attached. Similarly, some aporphine compounds of the invention, as shown in Formula A above, may have $R_6$ and $R_7$ jointly form a five membered-ring 1,3-dioxolane fused with the aromatic ring.

In a similar manner, the core moiety of the oxoaporphine compounds of the invention may be represented with a common Formula B shown below:

Formula B

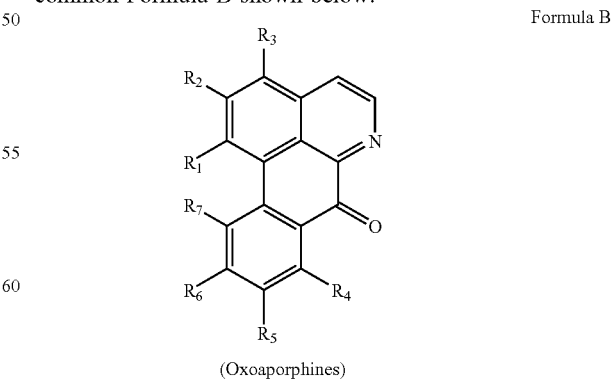

(Oxoaporphines)

where $R_1$, $R_2$, $R_5$ and $R_6$ are each selected from H, OH, O-acyl, OMe, OEt, O$^n$Pr and O$^i$Pr; $R_3$ and $R_4$ are each selected from H, OH, O-acyl, OMe, F, Cl, Br, $NO_2$ and CN; and $R_7$ is selected from H, OH, O-acyl, and OMe.

Some oxoaporphine compounds of the invention, as shown in Formula B above, may have $R_1$ and $R_2$ jointly form —$OCH_2O$— such that they form a five membered-ring 1,3-dioxolane fused with the aromatic ring to which they are attached. Similarly, some aporphine compounds of the invention, as shown in Formula B above, may have $R_5$ and $R_6$ jointly form —$OCH_2O$— such that they form a five membered-ring 1,3-dioxolane fused with the aromatic ring.

Aporphine and oxoaporphine compounds of the invention can prevent ischemia induced damages and minimize any complication associated with ischemia. Table 2, which summarizes results from i.v. administration of Compound 16, clearly shows that Compound 16 is effective in preventing or minimizing the ischemia-reperfusion induced arrhythmia.

TABLE 2

Effect of iv infusion of Compound 16 on reperfusion induced arrhythmia in rats.

|  | Ventricular tachycardia | | Ventricular fibrillation | | Mortality |
|---|---|---|---|---|---|
|  | Incident (%) | Duration (sec) | Incident (%) | Duration (sec) | (%) |
| vehicle | 100 | 46.6 ± 17.5 | 80 | 124.2 ± 25.9 | 80 |
| 0.5 ug/kg | 92 | 23.3 ± 4.8 | 85 | 111.5 ± 24.4 | 62 |
| 5 ug/kg | 91 | 27.9 ± 7.9 | 82 | 72.2 ± 22.9 | 46 |
| 50 ug/kg | 85 | 9.8 ± 8.8 | 54 | 42.3 ± 18.6 | 23* |

Data are presented as means + SE (n = 10-13);
*p < 0.05, as compared with the vehicle.
Vehicle is 0.01% DMSO in normal saline.

Furthermore, because of the relationship between endothelial dysfunction and insulin resistance in Type II diabetes, the fact that the aporphines and oxoaporphines of the invention can improve the vascular function by preserving eNOS activity suggests that these compounds can also enhance glucose utilization to minimize insulin resistance and to reduce blood sugar levels. As shown in Table 3, Compound 16 and Compound 20 are effective in reducing serum glucose levels in Type II rat model (NIDDM rat).

TABLE 3

Compound 16 and Compound 20 effects on serum glucose levels in NIDDM rats.

| Compound (dose) | Percentage of change (%) | n |
|---|---|---|
| Vehicle (2.3% tartaric acid, 3% glucose, iv) | 0 | 5 |
| Compound 16 (3 mg/kg × 3 days, iv) | 22 ± 3.6% | 5 |
| Compound 20 (3 mg/kg, × 3 days iv) | 12 ± 3.5% | 5 |
| Metformin (100 mg/kg × 3 days, po) | 39 ± 1.6% | 5 |

These protective effects are seen not only in rats, but also in rabbits and pigs, suggesting that such protective effects are not animal specific. Since these animal models have been validated to have good correlation with human disease, one of ordinary skill in the art would appreciate that such therapeutic effects can also be expected in human.

TABLE 4

Compound 16 effects on ischemia-reperfusion rabbit mortality

|  | Total | Died at ischemia period | Died at reperfusion period | Mortality (%) |
|---|---|---|---|---|
| Control | 10 | 0 | 3 | 30 |
| 0.25 mg/kg | 3 | 0 | 1 | 33.3 |
| 2.5 mg/kg | 6 | 0 | 0 | 0 |

The fact that aporphines and oxoaporphines of the invention can prevent or minimize complications induced from ischemia-reperfusion suggest that these compounds can reduce the overall mortality rates from ischemia events. As shown in Table 4, Compound 16 at 2.5 mole/kg is effective in reducing ischemia induced mortality.

Figure 5A:
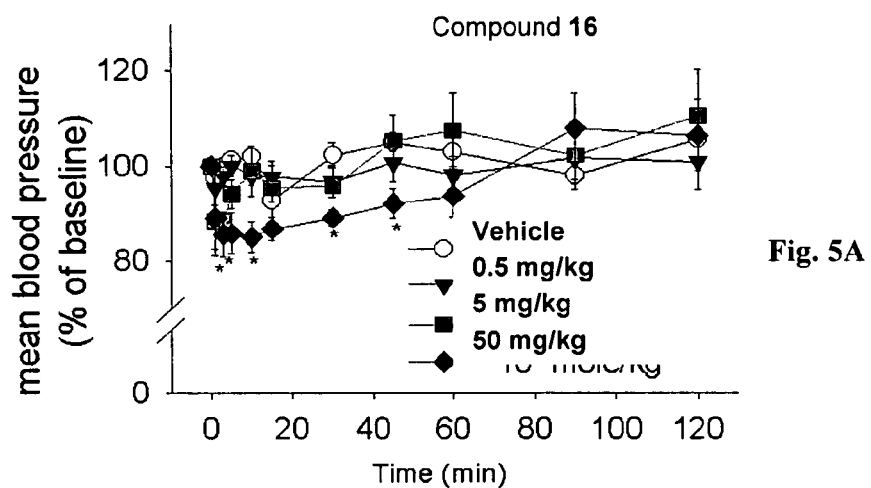
FIGS. 5A and 5B show that Compound 16, at therapeutic concentrations, does not have significant effects on mean blood pressure or heart rates in rats.
Figure 5B:
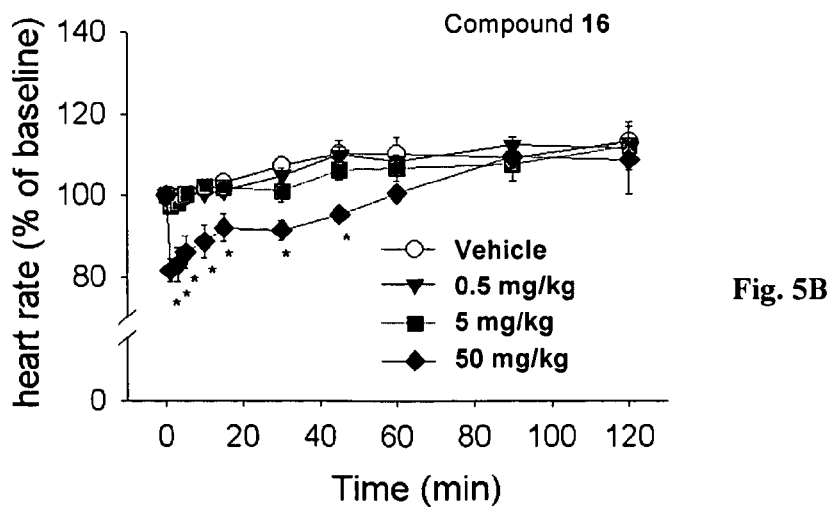

In addition, aporphines and oxoaporphines of the invention are found to have a satisfactory safe margin. They do not significantly affect the heart rates or blood pressure at therapeutically effective concentrations. FIGS. 5A and 5B show that at 0.5 mg/kg to 50 mg/kg, Compound 16 has no significant effects on blood pressure (FIG. 5A) or heart rate (FIG. 5B) in rats. However, at higher concentration, 50 mg/kg, Compound 16 decreased the heart rates to 81.5±2.8% of baseline values (from 361.5±9.3 bpm to 295.4±16.8 bpm; p<0.05), and the heart rates recovered after 45 minutes of drug application. Compound 16 at 50 mole/kg also decreased the mean blood pressure from 74.6±5.7 mmHg to 62.9±2.2 mmHg at 3 minutes after drug administration. The blood pressure decrease lasted for about 45 minutes. These results suggest that Compound 16 and other aporphine and oxoaporphine compounds at effective doses (e.g., 0.5 mg/kg) would not have significant impact on hemodynamic parameters. Similar results were obtained in rabbits, and no animals died in tests with 10-100 times the effective dose of Compound 16, suggesting this drug has a large safety margin.

The above examples show that the aporphine and oxoaporphine compounds of the invention are useful for the treatment of diseases associated with vascular dysfunction. Such protective effects are not limited to coronary vascular system, but also peripheral vascular system in other tissues and organs, such as brain and kidney.

All of the compositions of the invention can reduce or prevent complications associated with vascular dysfunction in various organs and tissues, such as brain, heart, and kidney. Complications induced by ischemia diseases may include ischemic cerebral thrombosis, ischemic cerebral embolism, hypoxic ischemic encephalopathy, ischemic cardiac disease or ischemic enteropathy, as well as ischemic cerebral apoplexy. Complications induced by metabolic disease may include diabetes-induced vascular diseases, such as hypertension, atherosclerosis, hyperglycemia, peripheral artery or venous thrombosis, retinopathy and nephropathy.

Various aporphines and oxoaporphines (see FIG. 3) have been used in the experiments described herein. These diverse compounds have different substituents on the same core aporphine or oxoaporphine moiety. The fact that they all have the same effects indicate that it is the aporphine core and oxoaporphine core that is critical for the pharmacological effects described here. Therefore, aporphine and oxoaporphine compounds that can be used to practice the invention are not limited to specific examples described above.

Any of the above-mentioned Formula A or B compounds can be used in combination or with a pharmaceutical acceptable carrier or excipient. Any carrier or excipient known in the art or commonly used in pharmaceuticals may be used with embodiments of the invention.

Materials and Experimental Procedures

The following describe some standard procedures used in testing the aporphine and oxoaporphine compounds of the invention. The description of these procedures is for illustration only. One of ordinary skill in the art would appreciate that some of these procedures may be substituted with similar procedures known in the art. Furthermore, the following may use a specific aporphine or oxoaporphine to illustrate the procedures. However, mentioning of a specific compound is only for convenience or clarity of description. One of ordinary skill in the art would appreciate that other aporphine and oxoaporphine compounds of the invention may be tested in a similar manner.

Evaluation of Infarct Size in a Rat Model of Regional Myocardial Ischemia and Reperfusion Seventy two male Wistar rats (215-300 g, Charles River, Margate, U.K.) were anaesthetized with thiopentone sodium (Intraval®, 120 mg/kg i.p.; Rhone-Merrieux, Essex, U.K.). The rats were tracheotomised and ventilated with a Harvard ventilator (70 strokes/min, tidal volume: 8-10 ml/kg, inspiratory oxygen concentration: 30%). Body temperature was maintained at 38±1° C. The right carotid artery was cannulated and connected to a pressure transducer (MLT 844, AD Instruments Ltd, Hastings, UK) to monitor mean arterial blood pressure and heart rate, which were continuously recorded on a data acquisition system (Powerlab® Version 4.0.4, AD Instruments, Hastings, UK) installed on a Dell Dimension 4100 personal computer, throughout the experiment. The right jugular vein was cannulated for the administration of test compound and Evans Blue dye (at the end of the experiment). A parasternal thoracotomy was performed, the heart was suspended in a temporary pericardial cradle and a snare occluder was placed around the left anterior descending coronary artery (LAD). After completion of the surgical procedure the animals were allowed to stabilize for 30 min before LAD ligation. The coronary artery was occluded at time 0 by tightening of the occluder. After 25 min of acute myocardial ischemia, the occluder was released to allow reperfusion for 2 h.

The test compounds were administered as a slow intravenous injection (i.v.) 5 min prior to the onset of reperfusion of the ischemic heart. Following the 2 h reperfusion period, the coronary artery was re-occluded and Evans Blue dye (1 ml of 2% w/v) was injected into the left ventricle, via the right jugular vein cannula, to distinguish between perfused and non-perfused (AAR) sections of the heart. The Evans Blue solution stains the perfused myocardium, while the occluded vascular bed remains uncolored. The animals were sacrificed with an overdose of anesthetic and the heart excised. The heart was sectioned into slices of 3-4 mm thick, the right ventricular wall was removed, and the AAR (pink) was separated from the non-ischemic (blue) area. The AAR was cut into small pieces and incubated with p-nitroblue tetrazolium (NBT, 0.5 mg/ml) for 40 min at 37° C. In the presence of intact dehydrogenase enzyme systems (viable myocardium), NBT forms a dark blue formazan, whilst areas of necrosis lack dehydrogenase activity and therefore fail to stain. Pieces were separated according to staining and weighed to determine the infarct size as a percentage of the weight of the AAR.

Experimental Groups

To elucidate the effects of the test compounds on the infarct size caused by regional myocardial ischemia and reperfusion, all animals were randomized into 8 study groups. The first group (Sham) comprised of animals not subjected to regional myocardial ischemia (25 min) followed by reperfusion (2 h) and treated with vehicle (1 ml/kg) 5 minutes prior to the onset of reperfusion. The second group of animals were subjected to regional myocardial ischemia (25 min) followed by reperfusion (2 h) and were treated with vehicle (saline, 1 ml/kg). The third group of animals were subjected to regional myocardial ischemia (25 min) followed by reperfusion (2 h) and were treated with vehicle (0.25% L-tartaric acid and 5% glucose, 1 ml/kg). The fourth, fifth and the sixth group of animals were subjected to regional myocardial ischemia (25 min) followed by reperfusion (2 h) and were treated with Compound 16 (0.15, 0.5 or 1.5 mg/kg respectively), 5 minutes prior to the onset of reperfusion. The last group of animals were subjected to regional myocardial ischemia (25 min) followed by reperfusion (2 h) and were treated with Compound 20 (0.5 mg/kg), 5 minutes prior to the onset of reperfusion. All animals were administered a saline infusion of 2 ml/kg/h throughout the reperfusion period.

Western Blot Analysis for eNOS Protein Determination

Hearts were pulverized at −80° C. using liquid nitrogen and a stainless steel pestle and mortar. The resulting powder was resuspended in homogenizing buffer (50 mM Tris-HCl, 150 mM NaCl, 1% Triton X-100, 2mM EDTA, 8mM EGTA, and 1 µg/ml.benzamidine, leupeptin, antipain, and aprotinin). The samples were centrifuged at 9000 rpm for 15 minutes at 4° C. The supernatants were retained, aliquoted and stored at −20° C. Total protein concentrations were determined using the Bradford method (Bio-Rad, UK). Samples were mixed with 5× Laemmli's loading buffer (final concentration Tris-HCl 0.05M, 6% glycerol, 0.002% bromophenol blue, 1.7% SDS (sodium dodecyl sulfate) and 1.55% DTT) and reduced by boiling for 3 min. 20 µg of protein from each sample were resolved on an 8% (w/v) SDS-polyacrylamide gel (0.75 mm thick) by electrophoresis (Mini-Protean III, Bio-Rad, USA). The gels were run at 90 V for 25 min followed by 120 V for 50 min, until the dye front reached the edge of the gel. Separated proteins were transferred onto nitrocellulose membrane by semi-dry transfer (Amersham Biosciences, UK) for 1 h 15 min at 100 mA/gel. Membranes were blocked for 1 hour at room temperature, with gentle rocking in 5%(w/v) non-fat milk (Marvel®, UK) in Tween buffer containing 10 mM Tris HCl (pH 7.6), 10 mM NaCl, and Tween 20 (20% w/v) to reduce non-specific binding. Membranes were then incubated overnight at 4° C. with a primary antibody specific for eNOS (NOS3 (C-20) rabbit polyclonal antibody; ½000 dilution) (Santa Cruz Biotechnology). Membranes were washed 3 times every 15 minutes by gently rocking in Tween buffer. Then following incubation with a goat anti-rabbit horseradish peroxidase-linked secondary antibody (½000) (DakoCytomation, Denmark) for 1 hour, with gentle rocking at room temperature membranes were washed with Tween buffer (3×5 min). Signals were detected using the enhanced chemiluminescence (ECL™) detection system (Cell Signaling Technology, U.S.A.) and autoradiographic film. For quantification of protein expression all blots were reprobed for muscle α-actin expression using ½000 dilution of a mouse anti-human actin (muscle antibody (Serotec), followed by incubation with a goat anti-mouse HRP linked secondary antibody (½000 dilution) (DakoCytomation, Denmark). Densitometry analysis was performed on scanned images (Hewlett Packard Scanjet) and analyzed using Scion Image (Scion Corp, National Institutes of Health, Bethesda, Md.).

Langendorff Heart Model

Adult male Wistar rats weighing 275-325 g, were intraperitoneally anesthetized with sodium pentobarbital (50 mg·kg$^{-1}$) and given heparin (300 Ukg·kg$^{-1}$) by the same route. Hearts were rapidly excised and immersed in 37° C. perfusion medium. The aorta was cannulated and retrograde-perfused at 80 mmHg with Tyrode's solution containing 120 mM NaCl, 25 mM NaHCO$_3$, 3 mM KCl, 1.2 mM NaH$_2$PO$_4$, 2.5 mM CaCl$_2$, 1.2 mM MgCl$_2$, and 1.2, and 5.5 mM glucose. The perfusate was equilibrated with 95% O$_2$, 5% CO$_2$ at 37° C. Perfusion pressure was monitored using a MLT844/D pressure transducer (Capto, Horten, Norway) connected to a PowerLab (ADInstruments, Castle Hill, Australia). The coronary effluent was collected for the measurement of coronary flow.

Plasma Glucose Determination in Lepr db Mouse

Test compound is administered i.v. once daily for three consecutive days to groups of 5 non-insulin dependent diabetic mellitus (NIDDM) male mice (C57BLKS/J-.+/+ Lepr db) weighting 50+10 gm (10-15 weeks old; serum glucose=500+50 mg/dl, serum insulin=13.0+2 ng/ml). All animal are allowed free access to normal laboratory chow and water.

Serum glucose level is determined by enzymatic method (Mutaratase-GOD) from orbital sinus blood samples obtained before and 90 minutes after the last vehicle and treat compound administered and percent change is determined. Serum glucose of post-treatment relative to pre-treatment group values obtained on the third day are calculated.

The effects in Ischemia-Induced Arrhythmia and Hemodynamic Effects in Rats

Opened-chest SD (Sprague-Dawley) anesthetized rats underwent myocardial ischemia by 5 min-occlusion of the left main coronary artery and followed by 30 min-reperfusion. During the myocardium reperfusion period, heart rate, blood pressure and EKG changes were recorded. Ventricular ectopic activity was evaluated according to the diagnostic criteria advocated by the Lambeth Convention. The incidences and durations of ventricular tachycardia and ventricular fibrillation were determined.

Statistical Analysis.

All data are presented as mean±s.e. mean of n observations, where n represents the number of animals studied. Infarct size was analyzed by 1-factorial ANOVA, followed by a Dunnett's test for comparison of a treated group to the vehicle. Hemodynamic data was analysed by 2-way ANOVA followed by a Bonferroni's test. A P-value of less than 0.05 was considered to be statistically significant.

The above describes various aporphine and oxoaporphine compounds and their treatment effects. The following examples describe the preparations of the aporphine and oxoaporphine compounds in accordance with embodiments of the invention.

EXAMPLE 1

Preparation of 2,9-Diisopropyloxy-1,10-dimethoxy-7-oxoaporphine (3), the formula B compound, wherein $R_1=R_6=$OMe, $R_2=R_5=$OiPr, $R_3=R_4=R_7=$H; and 9-Hydroxy-2-isoproploxy-1,10-dimethoxy-7-oxoaporphine (4), the formula B compound, wherein $R_1=R_6=$OMe, $R_2=$OiPr, $R_3=R_4=R_7=$H, $R_5=$OH.

1. Preparation of 2,9-Diisopropyloxy-1,10-dimethoxy-N-methylaporphine (2), the formula A compound, wherein $R_1=R_7=$OMe, $R_2=R_6=$O$^i$Pr, $R_3=R_5=R_8=$H, $R_4=$Me.

The mixture of boldine (1) (1.63 g, 5 mmol), anhydrous alcohol (50 ml), and anhydrous potassium carbonate (3.0 g) in a 250 ml round bottom flask was stirred in an oil bath (70° C.). A solution of 2-iodopropane (3.4 g, 20 mmol) in anhydrous alcohol solution (10 ml) was added dropwise over 1 hour. The reaction was allowed to proceed for 8 hours and then the solution was cooled to room temperature. The inorganic sediments were filtered and washed with alcohol. The combined filtrate and washings were concentrated under reduced pressure. The residue obtained was dissolved in chloroform (150 ml), then extracted successively with 10% sodium hydroxide solution (50 ml) and water (50 ml×3) to remove the impurity. The chloroform layer was dried with anhydrous sodium sulfate and concentrated under reduced pressure to give a residue, which was purified on a basic alumina column, and eluted with chloroform to obtain 2,9-diisopropyloxy-1,10-dimethoxy-N-methylaporphine (2) (1.54 g, 75% yield): $^1$H NMR (200 MHz, CDCl$_3$) δ 1.40 (6H, d, J=6.1 Hz, 2×CH$_3$), 1.43 (6H, d, J=6.2 Hz, 2×CH$_3$), 2.52 (3H, s, NCH$_3$), 3.64 (3H, s, 1-OCH$_3$), 3.85 (3H, s, 10-OCH$_3$), 4.54 (1H, m) and 4.59 (1H, m) (2×OCH), 6.56 (1H, s, H-3), 6.76 (1H, s, H-8), 8.06 (1H, s, H-11).

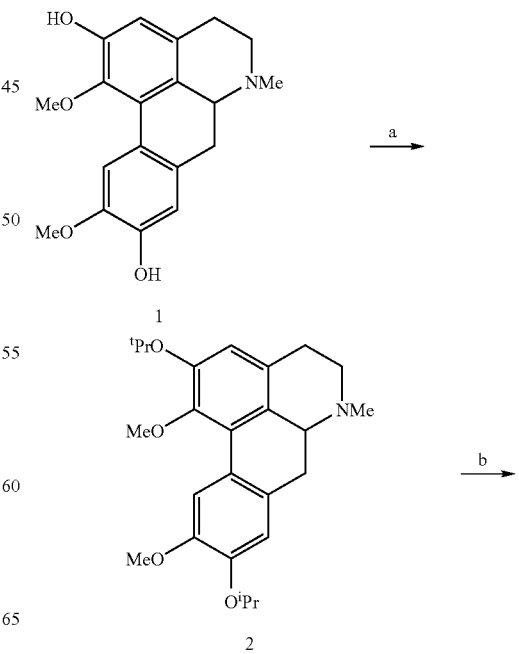

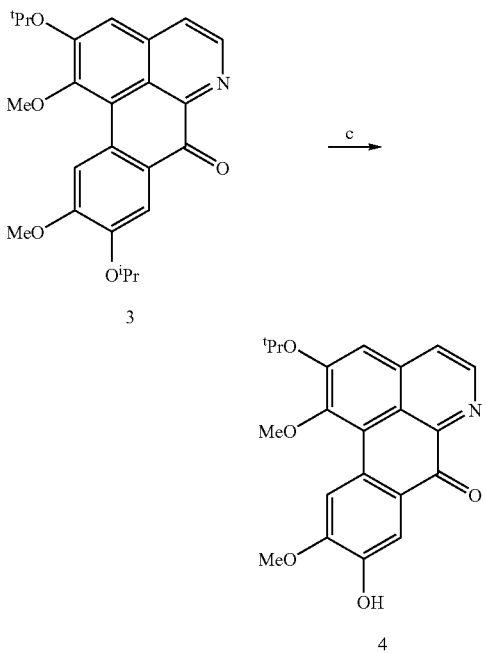

a. $^iPrI/K_2CO_3$, abs. EtOH, 70° C., 8 hr, 75%; b. Pb(OAc)$_4$, HOAc, rt, 12 hr, 50%; c. 4% H$_2$SO$_4$—HOAc, N$_2$, Δ, 1 hr, 22%.

2. Preparation of 2,9-diisopropyloxy-1,10-dimethoxy-7-oxoaporphine (3), a formula B compound, wherein $R_1=R_6=$OMe, $R_2=R_5=$O$^i$Pr, $R_3=R_4=R_7=$H.

To a solution of compound (2) (137 mg, 330 μM) in acetic acid (5 ml) was added lead tetraacetate (95%, 483 mg, 1.09 mmol). The reaction mixture was stirred for 12 hours at room temperature, then water (150 ml) was added, followed by successive extraction with chloroform (50 ml×4). The combined chloroform layers were washed successively with saturated sodium bicarbonate aqueous solution (50 ml), 10% sodium hyposulfite aqueous solution (50 ml) and water (50 ml×2), dried with anhydrous sodium sulfate, and concentrated under reduced pressure. The residue obtained was purified on a silica gel column and eluted with chloroform to give 2,9-diisopropyloxy-1,10-dimethoxy-7-oxoaporphine (3) (68 mg, 50% yield): m.p. 82-84° C.;IR(KBr)ν$_{max}$ 2976, 2933, 1654, 1590, 1563, 1508, 1459, 1431, 1416, 1359, 1296, 1275, 1241, 1216, 1138, 1110, 1057, 1009, 995, 925, 887, 864, 782 cm$^{-1}$; $^1$H NMR(200 MHz, CDCl$_3$) δ 1.44 (6H, d, J=6.1 Hz, 2×CH$_3$), 1.53 (6H, d, J=6.1 Hz, 2×CH$_3$), 4.01 (3H, s, 1-OCH$_3$), 3.85 (3H, s, 10-OCH$_3$), 4.87 (2H, m) (2×OCH), 7.79 (1H, d, J=5.4 Hz, H-4), 7.96 (1H, s, H-8), 8.75 (1H, s, H-11), 8.86 (1H, d, J=5.4 Hz, H-5); $^{13}$C NMR(50 MHz, CDCl$_3$) δ 21.7 (2C, q), 21.9 (2C, q), 56.0 (q), 60.4 (q), 70.9 (d), 71.2 (d), 107.2 (d), 110.6 (d), 112.2 (d), 120.2 (s), 121.3 (s), 123.2 (d), 126.7 (s), 128.8 (s), 135.4 (s), 145.9 (d), 145.3 (s), 147.8 (s), 151.5 (s), 154.6 (s), 154.8 (s), 181.3 (s); ESI MS (positive): [M+H]+408.

3: Preparation of 9-hydroxy-2-isopropyloxy-1,10-dimethoxy-7-oxoaporphine (4), a formula B compound, wherein $R_1=R_6=$OMe, $R_2=R_5=$O$^i$Pr, $R_3=R_4=R_7=$H.

The solution of compound (3) (50 mg) in acetic acid-sulfuric acid solution (96:4, 5 ml) was refluxed for 1 hour under nitrogen. After cooling to room temperature, the solution was evaporated under vacuum. The residue was neutralized with ammonia water and extracted with chloroform (100 ml×2). The combined chloroform layers were washed with water (50 ml×2), dried over anhydrous sodium sulfate, concentrated under reduced pressure. The residue obtained was purified on a silica gel column and eluted with chloroform-methanol (99:3) to obtain a brown solid, 9-hydroxy-2-isopropyloxy-1,10-dimethoxy-7-oxoaporphine (4) (10 mg, 22% yield): m.p. 240-242° C.; IR(KBr) ν$_{max}$ 3422, 3008, 2977, 2932, 1728, 1651, 1593, 1513, 1461, 1417, 1380, 1351, 1280, 1247, 1213, 1149, 1116, 1059, 1013, 932, 894, 866, 822 cm$^{-1}$; $^1$H NMR (200 MHz, CD$_3$OD) δ 1.51 (6H, d, J=6.0 Hz, 2×CH$_3$), 4.01 (3H, s, OCH$_3$), 4.02 (3H, s, OCH$_3$), 4.87 (1H, m, OCH), 7.25 (1H, s, H-3), 7.74 (1H, s, H-8), 7.83 (1H, d, J=4.8 Hz, H-4), 8.63 (1H, d, J=4.8 Hz, H-5), 8.68 (1H, s, H-11); ESI MS (positive): [M+H]$^+$366.

EXAMPLE 2

Preparation of 1,10-dimethoxy-7-oxoaporphine (7), a formula B compound, wherein $R_1=R_6=$Me, $R_2=R_3=R_4=R_5=R_7=$H.

1. Preparation of 1,10-dimethoxy-N-methylaporphine (6), a formula A compound, wherein $R_1=R_7=$OMe, $R_2=R_3=R_5=R_6=R_8=$H, $R_4=$Me.

Boldine [(1), 10.0 g, 30.58 mmol], acetonitrile (350 ml), anhydrous potassium carbonate (8.4 g, 61 mmol) and 5-chloro-1-phenyltetrazole (TzCl, 12.14 g, 33.64 mmol) were placed in a 500-ml round bottom flask in sequence. The mixture was heated under reflux for 24 hours. After cooling to room temperature, the insoluble inorganic salts were removed by filtration, and the sediment was washed with acetonitrile. The filtrate and acetonitrile washings were concentrated under reduced pressure to give a residue, which was suspended in chloroform (400 ml) and then extracted with water (200 ml×2) to remove the impurity. The chloroform layer, after being dried with anhydrous sodium sulfate, was concentrated. The residue was purified on a silica gel column (500 g) and eluted with chloroform-methanol (99:1) to give 2,9-O-bis(1-phenyltetrazol-5-yl)-1,10-dimethoxy-N-methylaporphine (5) (18 g, 96% yield):$^1$H NMR (400 MHz, CDCl$_3$) δ 2.55 (3H, s, NCH$_3$), 3.46 (3H, s, 1-OCH$_3$), 3.76 (3H, s, 10-OCH$_3$), 7.19 (1H, s, H-3), 7.31 (1H, s, H-8), 7.42-7.60 (6H, m), and 7.83-7.87 (4H, m) (C$_6$H$_5$×2), 8.04 (1H, s, H-11).

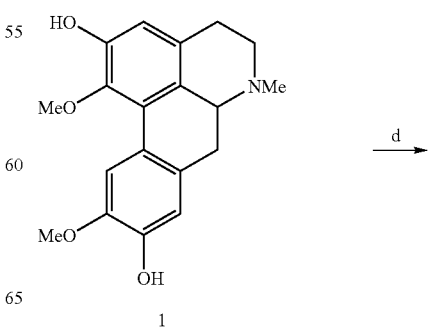

1

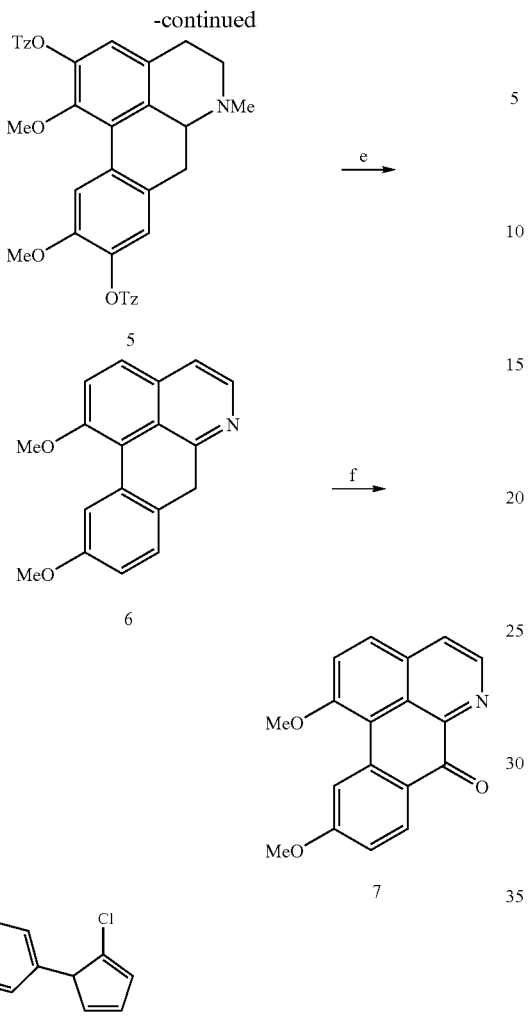

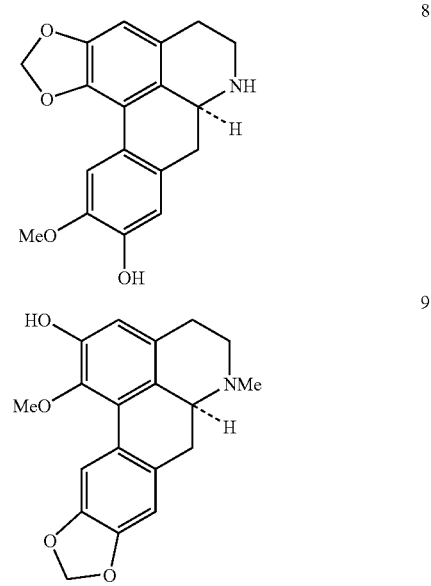

d. TzCl/K$_2$CO$_3$, MeCN, Δ, 24 hrs, 96%; e. 10% Pd-C, H$_2$ (120 psi), HOAc, 50° C., 3 d, 90%;

f. Tl(OAc)$_3$, HOAc, 70° C., 1 hr, 69%.

To a solution of compound (5) (8 g) in acetic acid (55 ml) was added palladium carbon (10%, 1 g). The suspension was catalytically hydrogenated (H$_2$, 120psi) at 50° C. for 3 days. After cooling, the reaction mixture was filtered through a Celite pad and the sediment was washed with chloroform. The combined filtrate and washing were concentrated under reduced pressure. The residue obtained was dissolved in chloroform (200 ml), extracted with 10% sodium hydroxide aqueous solution (50 ml×2) and water (100×2) to remove impurities. The chloroform layer, after being dried with anhydrous sodium sulfate, was concentrated under reduced pressure to give a residue, which was purified on a silica gel column and eluted with chloroform-methanol (98:2) to give 1,10-dimethoxy-N-methylaporphine (6) (4.12 g, 90% yield): $^1$H NMR(200 MHz, CDCl$_3$) δ 2.55 (3H, s, NCH$_3$), 3.82 (3H, s, 1-OCH$_3$), 3.85 (3H, s, 10-OCH$_3$), 6.76 (1H, dd, J=2.7, 8.3 Hz, H-9), 6.87 (1H, d, J=8.5 Hz, H-2), 7.04 (1H, d, J=8.5 Hz, H-3), 7.16 (1H, d, J=8.3 Hz, H-8), 7.89 (1H, d, J=2.7 Hz, H-11); $^{13}$C NMR(50 MHz, CDCl$_3$) δ 28.3 (t), 33.6 (t), 43.7 (q), 53.1 (t), 55.3 (q), 55.7 (q), 63.1 (d), 110.9 (d), 112.1 (d), 114.7 (d), 121.9 (s), 125.2 (s), 128.1 (d), 128.3 (d), 128.6 (d), 133.0 (s), 136.2 (s), 155.0 (s), 158.1 (s).

2. Preparation of 1,10-Dimethoxy-7-oxoaporphine (7), a formula B compound, wherein R$_1$=R$_6$=Me, R$_2$=R$_3$=R$_4$=R$_5$=R$_7$=H.

To a solution of compound (6) (148 mg, 0.5 mmol) in acetic acid (10 ml) was added thallium triacetate (816 mg, 2 mmol). The reaction mixture was stirred at 70° C. for 1 hour and then water (150 ml) was added. The solution formed was extracted with chloroform (50 ml×4). The combined chloroform layers were washed successively with saturated sodium bicarbonate aqueous solution (50 ml), 10% sodium hyposulfite aqueous solution (50 ml) and water (50 ml×2), followed by drying with anhydrous sodium sulfate and concentration under reduced pressure. The residue obtained was purified on a silica gel column and eluted with chloroform-methanol (99:1) to give 1,10-dimethoxy-7-oxoaporphine (7) (100 mg, 69% yield): m.p. 162-164° C.; IR(KBr) $v_{max}$ 2934, 2839, 1644, 1617, 1584, 1540, 1484, 1455, 1406, 1373, 1351, 1325, 1255, 1169, 1119, 1048, 1025, 985, 859, 810 cm$^{-1}$; $^1$H NMR (400 MHz, CDCl$_3$-CD$_3$OD, δ$_{CHCl3}$ 7.24) δ 3.79 (3H, s, 10-OCH$_3$), 4.04 (3H, s, 1-OCH$_3$), 16.88 (1H, dd, J=2.4, 8.8 Hz, H-9), 7.47 (1H, d, J=9.2 Hz, H-2), 7.73 (1H, d, J=4.7 Hz, H-4), 7.77 (1H, d, J=9.2 Hz, H-3), 8.29 (1H, d, J=8.8 Hz, H-8), 8.35 (1H, d, J=2.4 Hz, H-11), 8.64 (1H, d, J=4.7 Hz, H-5); $^{13}$C NMR (100 MHz, CDCl$_3$-CD$_3$OD, δ$_{CHCl3}$ 77.0) δ 55.2 (q), 56.3 (q), 112.3 (s), 113.5 (d), 113.8 (d), 119.7(d), 124.9 (d), 125.0 (s), 125.9 (s), 130.7 (d), 130.8 (d), 132.3 (s), 136.6 (s), 141.8 (d), 144.6 (s), 159.0 (s), 164.2 (s), 180.7 (s); ESI MS (positive): [M+Na]$^+$314.

EXAMPLE 3

Isolation of 1,2-methylenedioxy-9-hydroxy-10-methoxynoraporphine (8), a formula A compound, wherein R$_3$=R$_4$=R$_5$=R$_8$=H, R$_6$=OH, R$_7$=OMe, R$_1$ and R$_8$ jointly form —OCH$_2$O—

Dried wood fragments of Neolitsea konishi (16.8 kg) were extracted with 95% ethanol (45 L) four times. The ethanol extracts were combined and concentrated to yield an extract. The extract was added to warm water (60° C., 0.7 L×3) and 0.1 N hydrochloric acid (1L×4), and the mixture was agitated vigorously. The acidic solution was washed with chloroform (IL×2). The aqueous layer was neutralized with ammonia water to pH 9.0, and extracted with chloroform (1 L×3). The chloroform extracts were combined and dried with anhydrous sodium sulfite. After filtering, the organic layer was evaporated to afford an alkaloid mixture (9.78 g). The mixture was extracted with chloroform (150 mL) and 1 N NaOH (aq.) (80 mL×4), and the two layers were separated. The aqueous layer was neutralized with ammonia chloride to pH 9.0 and extracted with chloroform (200 mL×4). After the organic layer was evaporated, a phenolic alkaloid mixture (8.09 g) was obtained. The phenolic mixture was separated by circle chromatography using the delivery system ($CHCl_3$: $CH_3OH$:1%AcOH=2:2:1), and ten portions were obtained. The fourth portion (296 mg) was purified with flash chromatography (silica gel 14 g) using a mobile phase consisting of toluene containing 20% to 50% acetone. 1,2-methylenedioxy-9-hydroxy-10-methoxynoraporphine (8) (71 mg) was obtained. $R_f$ 0.44 ($Me_2CO$-toluene 3:2, saturated with $NH_4OH_{aq}$); $[\alpha]_D^{27}$+56.8 (c 0.95, $CHCl_3$); $^1H$ NMR (80 MHz, $CDCl_3$) δ 7.60 (1H, s, H-11), 6.76 (1H, s, H-8), 6.50 (1H, s, H-3), 6.00 (1H, d) and 5.90 (1H, d) (J=1.4 Hz, 1-$OCH_2O$-2), 3.90 (3H, s, 10-OMe); EIMS m/z (rel. int. %) $M^+$311 (21), 309 (100), 296 (2), 282 (4).

EXAMPLE 4

Isolation of 1-methoxy-2-hydroxy-9,10-methylenedioxyaporphine (9), a formula A compound, wherein $R_3=R_5=R_8$=H, $R_2$=OH, $R_1$=OMe, $R_4$=Me, $R_6$ and $R_7$ jointly form —$OCH_2O$—

The ethanol extract (326 g) from the stem of Litsea cubeba (8.5 kg) was added into hexane (0.5 L×2), warm water (60° C., 0.5 L×3) and 1 N hydrochloric acid (0.3 L×3), and the mixture was agitated vigorously. The acidic layer was neutralized with ammonia water to pH 9.0, and then extracted with chloroform (1 L×3). The organic layer was dried with anhydrous sodium sulfite to remove water. After evaporation, 11.36 g of an alkaloid mixture was obtained. The mixture was separated by circle chromatography using the delivery system ($CHCl_3$: $CH_3OH$:0.5%AcOH=2:2:1) and eight portions were obtained. The first portion (1.43 g) included the pure laurolitsine. The others were purified with flash chromatography using a mobile phase consisting of 0.5~2% methanol in a chloroform solution saturated with ammonia water. Isoboldine (21 mg), boldine (472 mg) and laurotetanine (25 mg) were obtained from the fourth portion of the chromatography. N-methyllaurotetanine (1.11 g), isoboldine (21 mg), boldine (472 mg) and laurotetanine (25 mg) were obtained from the sixth portion. The eighth portion was purified to provide isocorydine (12 mg). The fifth portion was purified to provide isoboldine (46 mg) and another mixture. This mixture was purified with flash chromatography using a mobile phase consisting of 40% acetone in toluene solution (saturated with ammonia water) and prepared TLC to obtain norisocorydine (66 mg), N-methyllaurotetanine (252 mg), N-methyllindcarpine (7 mg) and 1-methoxy-2-hydroxy-9,10-methylenedioxyaporphine (9) (5 mg): $R_f$ 0.50 ($Me_2CO$-toluene 13:7, saturated with $NH_4OH_{aq}$); $[\alpha]_D^{22}$+73.0 (c 0.83, $CHCl_3$); $^1H$ NMR (80 MHz, $CDCl_3$) δ 7.80 (1H, s, H-11), 6.74 (1H, s, H-8), 6.62 (1H, s, H-3), 5.95 (2H, s, 9-$OCH_2O$-10), 3.57 (3H, s, 1-OMe), 2.33 (3H, s, N-Me); EIMS m/z (rel. int. %) $M^+$325 (42), 324 (26), 310 (18), 43 (37), 42 (100).

EXAMPLE 5

Preparation of N-[2-(2-methoxyphenoxyl)]ethylnorthaliporphine (14), N-[2-(2-methoxy-phenoxyl)]ethylnorglaucine (16) and N-[2-(2-methoxyphenoxyl)] ethyllaurolitsine (19)

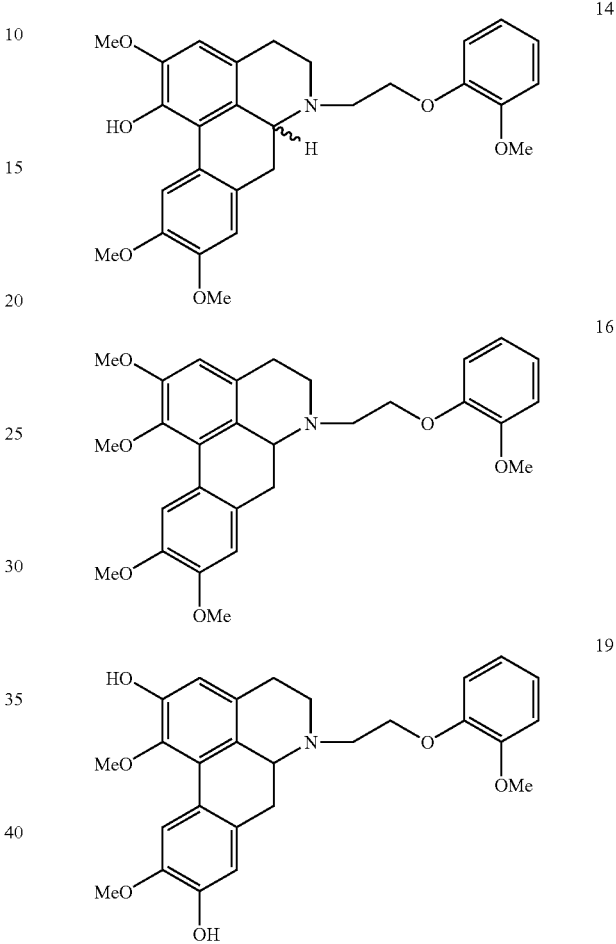

1. Preparation of N-formyllaurolitsine (10)

The wood collection (10 kg) of Phoebe formosana, collected from Nan-Tou, Taiwan, was cut into 2×2 $cm^2$ fragments and then extracted with 2% acetic acid solution (50 L, 40 L, 45 L; 80° C.). The extract was evaporated to afford crude laurolitsine 454 g (la). Fifty gram of crude laurolitsine, dimethylformamide (DMF, 250 mL), and ethyl formate (40 mL) were added into one 500-mL round bottle. The mixture was reacted at 90° C. After 60 hours, the solution was evaporated to remove DMF and extracted with chloroform (200 ml×4). The chloroform layers were combined and evaporated to dryness. The residue was crystallized from MeOH to obtain the pure N-formyllaurolitsine (10) (7.5 g): mp: 273-74° C.; UV: $\lambda_{max}$ nm (MeOH) (log ε) 283.6 (4.04), 303.2 (4.05); $^1H$ NMR ($CD_3OD$, 400 MHz) δ 8.61 and 8.41 (1H, s, N—CHO), 8.45 and 8.40 (1H, s, H-11), 7.21 and 7.16 (1H, s, H-8), 6.61 (1H, s, H-3), 3.58 (3H, s, 1-OMe), 3.89 (3H, s, 10-OMe); EIMS (70 eV): m/z (rel. int. %) 341 $M^+$(90), 296 (40), 283 (100), 240 (30), 58 (70).

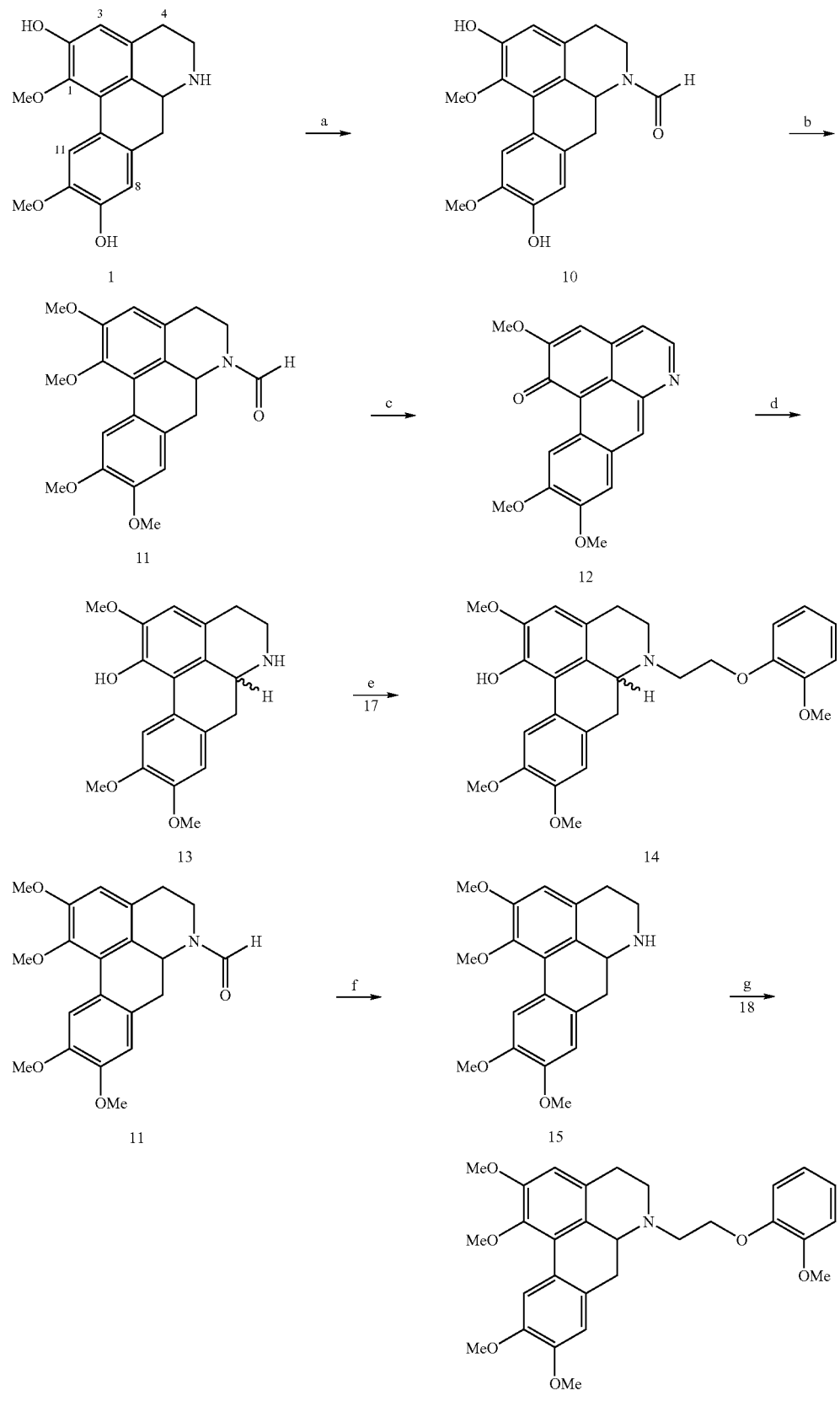

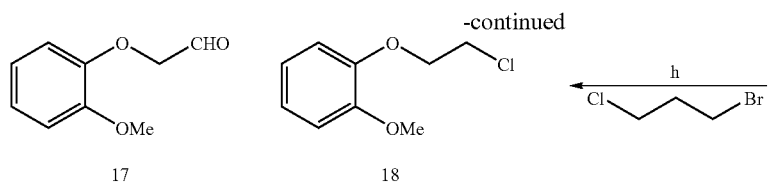
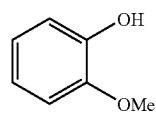

Reagents and Conditions a) HCO$_2$Et, DMF, 90° C., 60 h; b) MeI, K$_2$CO$_3$, MeOH, rt to 60° C., 24 h; c) 98% H$_2$SO$_4$, rt, 8 days; d) 5 bar H$_2$, Pt-C, AcOH, 48 h; e) NaBH$_3$CN, MeOH; f) KOH, EtOH, Δ, 3 h; g) 10%KOH$_{aq}$, Δ, overnight; h) 1.6N NaOH$_{aq}$, 100° C.

2. Preparation of N-Formylnorglaucine (11)

N-Formyllaurolitsine (10, 5 g, 0.015 mole), K$_2$CO$_3$ (2.5 g, 0.02 mole) and MeOH (50 ml) were added into a 250-mL two-neck round bottom flask. The mixture was reacted with methyl iodide (3.2 ml, 0.05 mole), added dropwise, for 30 minutes at room temperature. Then, the mixture was reacted at 60° C. After 24 hours, the mixture was evaporated to remove methanol, and the residue was partitioned with water (100 mL) and chloroform (100 mL×3). The chloroform layers were combined, dried with anhydrous sodium sulfite and evaporated to dryness. The residue (5.9 g) was purified by chromatography (silica gel: 70-230 mesh 180 g, mobile phase: CHCl$_3$) to obtain a colorless solid, N-formylnorglaucine (11) (4.70 g): Rf: 0.50; mp: 151-52; [α]D$^{25}$+ 309.6° (c 0.83, CHCl$_3$); UV:λ$_{max}$ nm (MeOH) (log ϵ) 281.2 (3.89), 301.6 (3.89); $^1$H NMR (CDCl$_3$, 400 MHz): δ 8.37 and 8.23 (1H, s, N—CHO), 8.11 and 8.12 (1H, s, H-11), 6.77 and 6.74 (1H, s, H-8), 6.62 and 6.59 (1H, s, H-3), 3.64 (3H, s, 1-OMe), 3.87 (3H, s, 2-OMe), 3.89 (3H, s, 9-OMe) and 3.88 (3H, s, 10-OMe); EIMS (70 eV): m/z (rel.int. %) M$^+$369 (5), 355 (100), 340 (40).

3. Preparation of Pancordine (12)

N-Formylnorglaucine (11, 2.2 g, 5.96 mmol) was added into a reactor with tight-closure. Then, 10 mL of 98% sulfuric acid was dropped into the reactor in an ice bath. The reactor was suctioned for 2 minutes and then closed tightly to allow reaction to occur in the dark at room temperature for 8 days. After opening the reactor, the reaction solution was poured into 100 mL ice water, and the mixture was stirred and adjusted with ammonia water to pH 8.0. The mixture was extracted with chloroform (100 mL×4), and the organic layers were collected. The organic portion was partitioned with water and saturated NaCl aqueous solution in sequence. After separation, the organic layer was dried with anhydrous sodium sulfite and evaporated to dryness. The residue (2.5 g) was purified by chromatography (silica gel: 230-400 mesh 75 g, mobile phase: MeOH/CHCl$_3$: 1/199) to obtain pancoridine (12) (950 mg, yield 50%): Rf 0.60 [CHCl$_3$-MeOH (9:1) with saturated ammonia water]; mp 211-213° C.; IR (KBr) ν$_{max}$ 3429 (br m), 2954 (m), 2831 (m), 1578 (s), 1531 (s), 1284 (s), 1121 (s), 1016 (m) cm$^{-1}$. $^1$H NMR (CD$_3$OD): δ 8.40 (1H, d, J=4.2Hz, H-5), 8.36 (1H, s, H-11), 7.65 (1H, s, H-7), 7.14 (1H, d, J=4.2Hz, H-4), 6.57 (1H, s, H-8) 6.47 (1H, s, H-3), 3.82 (3H, s, 2-OMe), 3.81 (3H, s, 9-OMe), 3.75 (3H, s, 10-OMe); EIMS [M]$^+$m/z 321 (100), 290 (100); HREIMS [M]$^+$m/z 321.0992 (cacld. for C$_{19}$H$_{15}$O$_4$N, 321.1001).

4. Preparation of Northaliporphine (13)

Pancoridine (12, 0.96 g, 3.0 mmol), glacial acid (60 mL) and 10% Pt-C (100 mg) were added into a high pressure hydrogenation reactor. After removing air, hydrogen gas was added and the mixture was reacted at 60° C. for two days. The mixture was filtered with silica gel after cooling. The residue on the silica gel was washed with acetone (200 mL) and the washings were collected. The filtrate and collected solvent were combined and evaporated to obtain a residue (1.95 g). The residue was purified by chromatography (silica gel: 230-400 mesh 60 g, mobile phase: 2-6% MeOH/CHCl$_3$.) to obtain northaliporphine (13) (600 mg, yield 60%): Rf 0.30 [CHCl$_3$-MeOH (9:1) with saturated ammonia water]; IR (KBr) ν$_{max}$ 3529 (br m), 2958 (m), 1605 (s), 1515 (s), 1463 (s), 1395 (s), 1339 (s), 1256 (s), 1112 (s) cm$^{-1}$; $^1$H NMR (CDCl$_3$, 400 MHz): δ 8.07 (1H, s, H-11), 6.72 (1H, s, H-8), 6.53 (1H, s, H-3), 3.88 (3H, s, 9-OMe), 3.88 (3H, s, 10-OMe), 3.88 (3H, s, 2-OMe); EIMS (70 eV): m/z (rel.int. %) M$^+$327 (70), 326 (100).

5. Preparation of N-[2-(2-methoxyphenoxyl)]ethylnorthaliporphine (14) (formula A, R$_3$=R$_5$=R$_8$=H, R$_2$=R$_5$=R$_7$=OMe, R$_1$=OH, R$_2$=2-(2-methoxyphenoxyl)ethyl)

Northaliporphine (5, 60 mg, 184 μmol), methanol (20 mL) and 2-(2-methoxy-phenoxy)-acetaldehyde (17, 53 mg, 280 μmol) were added into a 50-mL two-neck round bottom flask and stirred at room temperature. Sodium cyanoborohydride (20 mg) was added into the mixture in several portions, and the reaction was allowed to proceed for two days. The mixture was evaporated to dryness. The residue was partitioned with water (50 mL) and chloroform (50 mL×3), and the organic layers were collected. The chloroform layer was washed with water and saturated NaCl aqueous solution in sequence. After separation, the organic layer was dried with anhydrous sodium sulfate and then filtered. The filtrate was evaporated to dryness. The residue (69 mg) was purified by chromatography (mobile phase: 0-5% MeOH/CHCl$_3$. silica gel: 230-400 mesh 3 g) to obtain N-[2-(2-methoxyphenoxyl)]ethylnorthaliporphine (14) (51 mg; yield 58%): Rf 0.22 (2% MeOH—CHCl$_3$, saturated ammonia water); IR (KBr) ν$_{max}$ 3515 (m), 2936 (m), 1591 (s), 1505 (s) 1462 (s), 1395 (s), 1253 (s), 1092 (m) cm$^{-1}$, $^1$H NMR (CDCl$_3$, 400 MHz): δ 8.01 (1H, s, H-11), 6.91 (4H, m, 6'-9'H), 6.74 (1H, s, H-8), 6.53 (1H, s, H-3), 6.08 (1H, bs, 1-OH), 4.25 (2H, t, J=6.6 Hz), 3.90 (3H, s, 9-OMe), 3.89 (3H, s, 10-OMe), 3.88 (3H, s, 2-OMe), 3.62 (3H, s, 5'-OMe); $^{13}$C NMR (CDCl$_3$): δ 149.4 (s), 148.2 (s), 147.7 (s), 147.2 (s), 145.8 (s), 140.7 (s), 128.9 (s), 126.7 (s), 124.8 (s), 123.9 (s), 119.6 (s), 121.3 (d), 120.9 (d), 113.3 (d),112.2 (d), 111.9 (d), 111.0 (d), 108.8 (d), 66.7 (t), 60.2 (d), 56.2 (q), 56.0 (q), 55.8 (q), 55.8 (q), 55.7 (q), 53.3 (t), 50.7 (t), 34.7 (t), 29.4 (t); EIMS (70 eV): m/z (rel.int. %) [M]$^+$477 (52), 476 (17), 475 (20), 341 (25), 340 (100), 311 (41); HREIMS [M]$^+$ $^{m/z}$ 477.2148, (cacld for C$_{29}$H$_{31}$O$_6$N, 477.2151).

6. Preparation of O-(2-chloroethyl)guaiacol (18)

Guaiacol (6.2 g, 50 mmol) and 1-bromo-2-chloro-ethane (8.4 mL, 100 mmol) were mixed thoroughly and heated at 100° C. for 30 minutes. Then, 31 ml of 1.6 N NaOH aqueous solution was added into the mixture to bring the pH to about 7.0. After cooling, the mixture was extracted with chloroform. The chloroform layer was partitioned with 20% NaOH aqueous solution, water and saturated NaCl aqueous solution in sequence. The organic portion was dried with anhydrous sodium sulfite and evaporated to dryness to obtain O-(2-chloroethyl)guaiacol (18) (9 g; yield 96%). $R_f$ 0.67 (chloroform with saturated ammonia water); IR (KBr) $v_{max}$ 2934 (m), 1593 (s), 1504 (s), 1455 (s), 1254 (s), 1224 (s), 1178 (s), 1125 (s), 1028 (m) cm$^{-1}$; $^1$H NMR (CDCl$_3$, 400MHz): δ 6.94 (4H, m), 4.26 (2H, t, J=6.3Hz), 3.85 (3H, s, 2-OMe), 3.81 (2H, t, J=6.3Hz).

7. Preparation of Norglaucine (15)

Potassium hydroxide (2.38 g, 42.43 mmol), N-fomylnorglaucine (11, 1.02 g, 2.76 mmol) and ethanol (12 mL) were added into a 50-mL round bottom flask and stirred at room temperature. The mixture was heated slowly to 90° C. for 7 hours to complete the reaction. The mixture was evaporated to remove the solvents, and distilled water (50 mL) was added. The water portion was extracted with chloroform (50 mL×3), and the organic layers were collected. The organic portion was dried with anhydrous sodium sulfite, filtered and evaporated to dryness. The residue was purified by chromatography (mobile phase: 0-5% MeOH/CHCl$_3$. silica gel: 230-400 mesh 34 g) to obtain norglaucine (15) (682 mg; yield 72.5%): oily form, $R_f$ 0.28 (A); $[α]_D^{25}$+77.1° (c 0.35, CHCl$_3$); UV: $λ_{max}$ nm (MeOH) (log ε) 302.0 (2.88), 369.6 (2.14); $^1$H NMR (CDCl$_3$, 400 MHz): 68.09 (1H, s, H-11), 6.73 (1H, s, H-8), 6.58 (1H, s, H-3), 3.90 (3H, s, 9-OMe), 3.88 (3H, s, 10-OMe), 3.86 (3H, s, 2-OMe), 3.65 (3H, s, 1-OMe); EIMS (70 eV): m/z (rel.int. %) 341 M+(34), 328 (100).

8. Preparation of N-[2-(2-methoxyphenoxyl)]ethylnorglaucine (16) (formula A, $R_1$=$R_2$=$R_6$=$R_7$=OMe, $R_3$=$R_5$=$R_8$=H, $R_4$=2-(2-methoxyphenoxyl)ethyl)

Norglaucine (15, 1 g, 2.9 mmol), O-(2-chloroethyl)guaicol (18, 606 mg, 3.2 mmol) and 10% KOH aqueous solution (1 g in 10 ml) were added into 50 ml round bottom flask. The mixture was stirred and heated at 105-110° C. overnight. After cooling to room temperature, 50 ml of water was added into the solution. The solution was extracted with chloroform (100 mL×3,) and the organic layers were collected. The organic portion was partitioned with water and saturated NaCl aqueous solution. After separation, the chloroform layer was removed, dried with anhydrous sodium sulfite and then filtered. The filtrate was evaporated to dryness. The residue (1.5 g) was purified by chromatography using silica gel (31 g, 230-400 mesh) with an eluting solvent consisting of chloroform. Compound 16, N-[2-(2-methoxyphenoxyl)]ethylnorglaucine, was obtained (1.02 g, yield 71%). Rf 0.28 (2%MeOH—CHCl$_3$,saturated ammonia water); $[α]_D^{25}$ 24.0° (c 1.0, CHCl$_3$); UV: $λ_{max}$ nm (MeOH) (log ε) 302.0 (2.88), 369.6 (2.14); $^1$H NMR (CDCl$_3$, 400 MHz): δ 8.05 (1H, s, H-11), 6.89 (4H, m), 6.74 (1H, s, H-8), 6.57 (1H, s, H-3), 4.23 (2H, t, J=6.6Hz), 3.90 (3H, s, 9-OMe), 3.88 (3H, s, 10-OMe), 3.86 (3H, s, 2-OMe), 3.81 (3H, s, 1-OMe), 3.62 (3H, s, 5'-OMe); $^{13}$C NMR (CDCl$_3$) δ 151.9 (s), 149.4 (s), 148.(s), 148.0 (s), 147.4 (s), 144.3 (s), 129.4 (s), 129.0 (s), 128.7 (s), 127.5 (s), 124.5 (s), 121.2 (d), 120.8 (d), 113.2 (d), 111.8 (d), 111.6 (d), 110.8 (d), 110.4 (d), 66.8 (t), 60.2 (d), 55.9 (q), 55.9 (q), 55.8 (q), 55.7 (q), 55.7 (q), 53.3 (t), 50.7 (t), 34.8 (t), 29.4 (t); EIMS (70 eV): m/z (rel.int. %) M$^+$ 491 (71).476 (17), 489 (33), 355 (34), 354 (100), +352 (27); HREIMS [M]$^+$ m/z 491.2310, (cacld for C$_{29}$H$_{33}$O$_6$N, 491.2308).

9. Preparation of N-[2-(2-methoxyphenoxyl)]ethyllaurolitsine (19) (formula A, $R_1$=$R_7$=OMe, $R_2$=$R_5$=$R_8$=H, $R_2$=$R_6$=OH, $R_4$=2-(2-methoxyphenoxyl)ethyl)

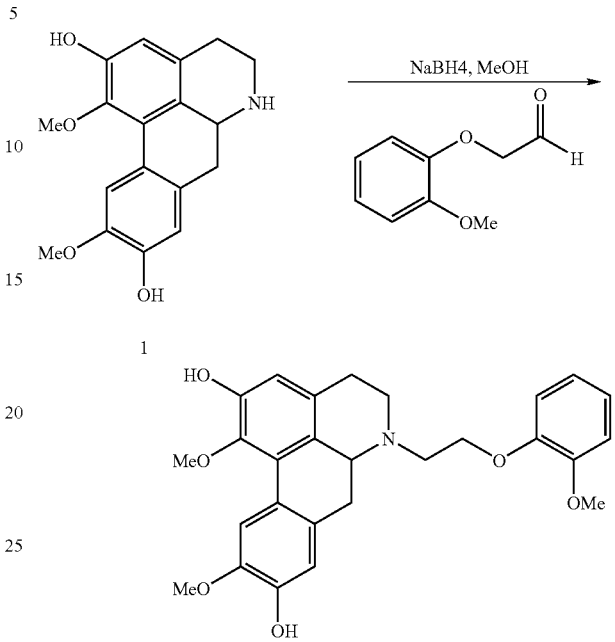

Laurolitsine (1a) (300 mg) was added into a 25 ml round bottom flask. MeOH (15 mL) and Guaiacol acetaldehyde ether (17, 166 mg, 1 mmol) were added into the same bottle. The mixture was stirred for 30 minutes at room temperature, and then NaBH$_3$CN (124 mg, 1.9 mmol) was added. After further stirring for 2.5 hours, the mixture was evaporated to remove MeOH. The residue was dissolved with EtOAc (50 mL) and then dried with anhydrous sodium sulfite. After filtration, the filtrate was evaporated to dryness. The residue was purified by flash chromatography (eluting solvent: 0-1% MeOH/CHCl$_3$, silica gel 70-230 mesh 15 g) to obtain compound 19 (200 mg): $^1$H-NMR (CDCl$_3$, 400 MHz) δ 7.86 (1H, s, H-11), 6.94-6.86 (4H, m, C$_6$H$_4$), 6.80 (1H, s, H-8), 6.63 (1H, s, H-3), 5.81 (2H, broad s, OH), 4.22 (2H, t, J=6.5 Hz, H-13), 3.89 (3H, s, OMe), 3.83 (3H, s, OMe), 3.56 (3H, s, OMe), 3.42-3.35 (2H, m, H-4), 3.22 (1H, dd, J=5.8 & 5.4 Hz), 3.06-2.98 (3H, m), 2.71-2.57 (2H, m); ESIMS m/z (rel. int. %) [M+H]+464 (45), 264 (90), 180 (20).

The invention provides aporphine and oxoaporphine compounds for preventing or treating ischemic and metabolic diseases or the induced complications, such as ischemia-induced damages or diabetes-associated vascular disorders. These compounds can thereby prevent or treat ischemic and metabolic diseases. There are no significant side effects to the patients during the treatment of the ischemic and metabolic diseases with the compounds. Thus, compounds of the invention produce excellent results. When compared with conventional methods in the art for opening up blood vessel by lysing the infarcted thrombus, compounds of the present invention have better therapeutic efficacies by reserving the endothelial nitric oxide synthase to maintain the vascular function.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An aporphine compound having the following structure:

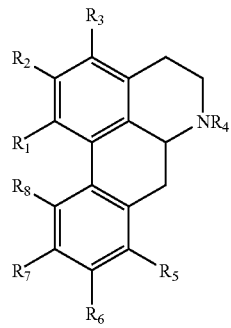

wherein $R_1$ and $R_2$ jointly form —$OCH_2O$—, or $R_6$ and $R_7$ jointly form —$OCH_2O$—,
wherein $R_3$ and $R_5$ are each selected from H, OH, O-acyl, OMe, F, Cl, Br, $NH_2$, $NO_2$ and CN; $R_8$ is selected from H, OH, and OMe; and $R_4$ is selected from allyl and $C_nH_{2n+1}$, $n \geq 2$; or $R_4$ is an alkylaryl group.

2. The aporphine compound of claim 1, wherein $R_1$ and $R_2$ jointly form —$OCH_2O$—.

3. The aporphine compound of claim 1, wherein $R_6$ and $R_7$ jointly form —$OCH_2O$—.

4. An aporphine compound having the following structure:

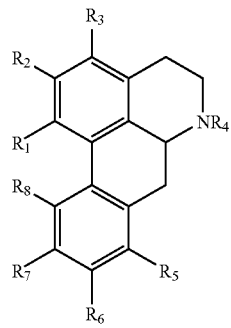

wherein $R_1$, $R_2$, $R_6$ and $R_7$ are each selected from H, OH, O-acyl, OMe, OEt, $O^nPr$ and $O^iPr$, or $R_1$ and $R_2$ jointly form —$OCH_2O$—, or $R_6$ and $R_7$ jointly form —$OCH_2O$—,
wherein $R_3$ and $R_5$ are each selected from H, OH, O-acyl, OMe, F, Cl, Br, $NH_2$, $NO_2$ and CN; $R_8$ is selected from H, OH, and OMe; and
wherein $R_4$ is an alkylaryl group selected from the group consisting of

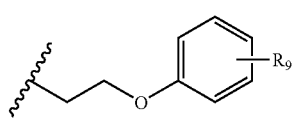

wherein $R_9$ is H, OH, $NO_2$, halide, or OAc;

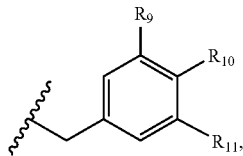

wherein $R_9$, $R_{10}$, $R_{11}$ are independently H, OH, OMe, $NO_2$, halide, OAc, or alkyl;

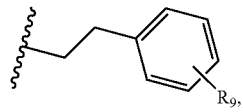

wherein $R_9$ is H, OH, OMe, $NO_2$, halide, or OAc; and

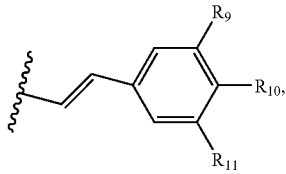

wherein $R_9$, $R_{10}$, $R_{11}$ are independently H, OH, OMe, $NO_2$, or OAc.

5. The aporphine compound of claim 4, wherein $R_1$ and $R_2$ jointly form —$OCH_2O$—.

6. The aporphine compound of claim 4, wherein $R_6$ and $R_7$ jointly form —$OCH_2O$—.

7. An oxoaporphine compound having the following structure:

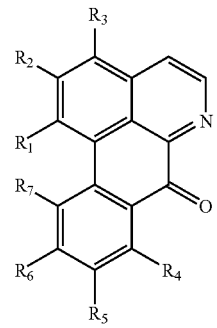

where $R_1$, $R_2$, $R_5$ and $R_6$ are each selected from H, OH, O-acyl, OMe, OEt, $O^nPr$ and $O^iPr$, or $R_1$ and $R_2$ jointly form —$OCH_2O$—, or $R_5$ and $R_6$ jointly form —$OCH_2O$—;
$R_3$ is selected from H, OH, O-acyl, OMe, F, Cl, Br, $NO_2$ and CN; $R_4$ is selected from OH, O-acyl, OMe, F, Cl, Br, $NO_2$ and CN; and $R_7$ is selected from H, OH, O-acyl, and OMe.

8. The oxoaporphine compound of claim 7, wherein $R_1$ and $R_2$ jointly form —$OCH_2O$—.

9. The oxoaporphine compound of claim 7, wherein $R_5$ and $R_6$ jointly form —$OCH_2O$—.

* * * * *